US010667718B2

(12) United States Patent
Griswold et al.

(10) Patent No.: US 10,667,718 B2
(45) Date of Patent: Jun. 2, 2020

(54) QUANTITATIVE PROSTATE CANCER IMAGING WITH MAGNETIC RESONANCE FINGERPRINTING (MRF)

(71) Applicant: Case Western Reserve University, Cleveland, OH (US)

(72) Inventors: Mark Griswold, Shaker Heights, OH (US); Vikas Gulani, Shaker Heights, OH (US); Chaitra Badve, Beachwood, OH (US); Yun Jiang, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1041 days.

(21) Appl. No.: 15/079,283

(22) Filed: Mar. 24, 2016

(65) Prior Publication Data
US 2016/0278661 A1 Sep. 29, 2016

Related U.S. Application Data

(60) Provisional application No. 62/138,458, filed on Mar. 26, 2015.

(51) Int. Cl.
*A61B 5/055* (2006.01)
*A61B 5/00* (2006.01)
(Continued)

(52) U.S. Cl.
CPC .............. *A61B 5/055* (2013.01); *A61B 5/004* (2013.01); *A61B 5/4381* (2013.01); *G01R 33/50* (2013.01);
(Continued)

(58) Field of Classification Search
CPC ..... A61B 2576/02; A61B 5/004; A61B 5/055; A61B 5/4381; G01R 33/50;
(Continued)

(56) References Cited

U.S. PATENT DOCUMENTS

| 2011/0020235 A1* | 1/2011 | Hurd ...................... A61B 5/055 424/9.3 |
| 2012/0112743 A1* | 5/2012 | Granlund ........... G01R 33/5614 324/309 |
| 2016/0282430 A1* | 9/2016 | Gulani ............... G01R 33/4828 |

OTHER PUBLICATIONS

American Cancer Society. Cancer Facts & Figures 2015. (American Cancer Society, Atlanta, 2015).
(Continued)

*Primary Examiner* — Mark D Remaly
(74) *Attorney, Agent, or Firm* — Quarles & Brady LLP

(57) ABSTRACT

Example embodiments associated with characterizing a sample using NMR fingerprinting are described. One example NMR apparatus includes an NMR logic that repetitively and variably samples a (k, t, E) space associated with an object to acquire a set of NMR signals that are associated with different points in the (k, t, E) space. Sampling is performed with t and/or E varying in a non-constant way. The NMR apparatus may also include a signal logic that produces an NMR signal evolution from the NMR signals and a characterization logic that characterizes a tissue in the object as a result of comparing acquired signals to reference signals. Example embodiments facilitate distinguishing prostate cancer tissue from normal peripheral zone tissue based on quantitative data acquired using NMR fingerprinting in combination with apparent diffusion co-efficient (ADC) values or perfusion values acquired using DWI-MRI or DCE-MRI.

18 Claims, 14 Drawing Sheets

(51) Int. Cl.
*G01R 33/563* (2006.01)
*G01R 33/561* (2006.01)
*G01R 33/50* (2006.01)
*G01R 33/565* (2006.01)

(52) U.S. Cl.
CPC ... *G01R 33/5613* (2013.01); *G01R 33/56341* (2013.01); *G01R 33/56366* (2013.01); *A61B 2576/02* (2013.01); *G01R 33/56563* (2013.01)

(58) Field of Classification Search
CPC .......... G01R 33/5613; G01R 33/56341; G01R 33/56366; G01R 33/56563
See application file for complete search history.

(56) References Cited

OTHER PUBLICATIONS

Aydin H, et al. Detection of prostate cancer with magnetic resonance imaging: optimization of T1-weighted, T2-weighted, dynamic-enhanced T1-weighted, diffusion-weighted imaging apparent diffusion coefficient mapping sequences and MR spectroscopy, correlated with biopsy and histopathological findings. J Comput Assist Tomogr. 2012;36(1):30-45.
Bittencourt LK, et al. Prostate MRI: diffusionweighted imaging at 1.5T correlates better with prostatectomy Gleason Grades than TRUS-guided biopsies in peripheral zone tumours. Eur Radiol. 2012;22(2):468-75.
Boesen L, et al. Apparent diffusion coefficient ratio correlates significantly with prostate cancer gleason score at final pathology. J Magn Reson Imaging. 2015;42(2):446-53.
Cookson MS, et al. Variation in the definition of biochemical recun-ence in patients treated for localized prostate cancer: the American Urological Association Prostate Guidelines for Localized Prostate Cancer Update Panel report and recommendations for a standard in the reporting of surgical outcomes. J Urol. 2007;177(2):540-5.
Costello LC, et al. Zinc inhibition of mitochondrial aconitase and its importance in citrate metabolism of prostate epithelial cells. J Biol Chem. 1997;272(46):28875-81.
Doneva, M., et al. "Compressed sensing for chemical shift-based water-fat separation." Magnetic resonance in medicine 64.6 (2010): 1749-1759.
Doneva, M., et al. "Compressed sensing reconstruction for magnetic resonance parameter mapping." Magnetic Resonance in Medicine 64.4 (2010): 1114-1120.
Draisma G, et al. Lead time and overdiagnosis in prostate-specificantigen screening: importance of methods and context. J. Natl. Cancer Inst. 2009;101(6):374-383.
Esen M, et al. Utility of ADC measurement on diffusion-weighted Mri in differentiation of prostate cancer, normal prostate and prostatitis. Quant Imaging Med Surg. 2013;3(4):210-6.
Garcia-Reyes, K, et al. Detection of prostate cancer with multiparametric MRI (mpMRI): effect of dedicated reader education on accuracy and confidence of index and anterior cancer diagnosis. Abdom Imaging. 2015;40(1):134-42.
Garner, Bryan A, A Dictionary of Legal Modem Legal Usage. Second Edition 1995, p. 624.
Gibbs P, et al. Correlation of ADC and T2 measurements with cell density in prostate cancer at 3.0 Tesla. Invest Radiol. 2009;z14(9):572-6.
Gibbs P, et al. Diffusion imaging of the prostate at 3.0 tesla. Invest Radiol. 2006;41(2):185-8.
Hambrock T, et al. Relationship between apparent diffusion coefficients at 3.0-T MR imaging and Gleason grade in peripheral zone prostate cancer. Radiology. 2011;259(2):453-61.
Jiang Y, et al. MR fingerprinting using fast imaging with steady state precession (FISP) with spiral readout. Magn Reson Med. 2014; doi: 10.1002/mrm.25559.
Jiang Y, et al. Simultaneous T1, T2, Diffusion and Proton Density Quantification with MR Fingerprinting. In: Proceedings of the 2014 Joint Annual Meeting of ISMRM-ESMRMMB; May 10-16; Milan, Italy. Abstract 0028.
Kim CK, et al. Diffusion-weighted imaging of the prostate at 3 T for differentiation of malignant and benign tissue in transition and peripheral zones: preliminary results. J Comput Assist Tomogr. 2007;31(3):449-54.
Liney GP, et al. In vivo quantification of citrate concentration and water T2 relaxation time of the pathologic prostate gland using 1H MRS and MRI. Magn Reson Imaging. 1997;15(10)1177-86.
Ma, Dan, et al. "Magnetic resonance fingerprinting." Nature 495. 7440 (2013): 187.
Mariotto AB, et al. Projections of the cost of cancer care in the United States: 2010-2020. J Natl Cancer Inst. 2011;103(2):117-28.
Mullerad, M, et al. Prostate cancer: detection of extracapsular extension by genitourinary and general body radiologists at MR imaging. Radiology. 2004;232(1):140-6.
Nagel KN, et al. Differentiation of prostatitis and prostate cancer by using diffusion-weighted MR imaging and MR-guided biopsy at 3 T. Radiology. 2013;267(1):164-72.
Oto A, et al. Diffusion-weighted and dynamic contrast-enhanced MRI of prostate cancer: correlation of quantitative MR parameters with Gleason score and tumor angiogenesis. AJR Am J Roentgenol. 2011;197(6):1382-90.
Park BK, et al. Comparison of phased-array 3.0-T and endorectal 1.5-T magnetic resonance imaging in the evaluation of local staging accuracy for prostate cancer. J Comput Assist Tomogr. 2007;31(4):534-8.
Peng Y, et al. Quantitative analysis of multiparametric prostate MR images: differentiation between prostate cancer and normal tissue and correlation with Gleason score—a computer-aided diagnosis development study. Radiology. 2013;267(3):787-96.
Pickles MD, et al. Diffusion-weighted imaging of normal and malignant prostate tissue at 3.0T. J Magn Reson Imaging. 2006;23(2):130-4.
Pokorny, MR, et al. Prospective study of diagnostic accuracy comparing prostate cancer detection by transrectal ultrasound-guided biopsy versus magnetic resonance (MR) imaging with subsequent MR-guided biopsy in men without previous prostate biopsies. Eur Urol. 2014;66(1):22-9.
Ruprecht, O., et al. MRI of the prostate: interobserver agreement compared with histopathologic outcome after radical prostatectomy. Eur J Radiol. 2012;81(3):456-60.
Shukla-Dave A, et al. Chronic prostatitis: MR imaging and 1H MR spectroscopic imaging findings—initial observations. Radiology. 2004;231(3):717-24.
Simpkin CJ, et al. Relationship between T2 relaxation and apparent diffusion coefficient in malignant and non-malignant prostate regions and the effect of peripheral zone fractional volume. Br J Radiol. 2013;86(1024):20120469.
Telesca D, et al. Estimating lead-time and overdiagnosis associated with PSA screening from prostate cancer incidence trends. Biometrics. 2008;64(1):10-9.
Turkbey B, et al. Prostate cancer: value of multiparametric MR imaging at 3 T for detection—histopathologic correlation. Radiology. 2010;255(1):89-99.
Ukimura, Coleman JA, et al. Contemporary role of systematic prostate biopsies: indications, techniques, and implications for patient care. Eur Urol. 2013;63(2):214-30.
Vos EK, et al. Multiparametric Magnetic Resonance Imaging forDiscriminating Low-Grade From High-Grade Prostate Cancer. Invest Radiol. 2015;50(8):490-7.
Vos EK, et al. Assessment of prostate cancer aggressiveness using dynamic contrast-enhanced magnetic resonance imaging at 3 T. Eur Urol. 2013;64(3):448-55.
Weis J, et al. MR spectroscopy of the prostate at 3T: measurements of relaxation times and quantification of prostate metabolites using water as an interna reference. Magn Reson Med Sci. 2013;12(4):289-96.
Wolf AM, et al. American Cancer Society guideline for the early detection of prostate cancer: update 2010. CA Cancer J Clin. 2010;60(2):70-98.

(56) References Cited

OTHER PUBLICATIONS

Woodfield CA, et al. Diffusion-weighted MRI of peripheral zone prostate cancer: comparison of tumor apparent diffusion coefficient with Gleason score and percentage of tumor on core biopsy. AJR Am J Roentgenol. 2010;194(4): W316-22.
Yamauchi FI, et al. Prostate cancer discrimination in the peripheral zone with a reduced field-of-view T2-mapping MRI sequence. Magn Reson Imaging. 2015;33(5):525-30.

* cited by examiner

US 10,667,718 B2

QUANTITATIVE PROSTATE CANCER IMAGING WITH MAGNETIC RESONANCE FINGERPRINTING (MRF)

CROSS REFERENCE TO RELATED APPLICATIONS

This application claims the benefit of U.S. Provisional Application 62/138,458 filed Mar. 26, 2015.

FEDERAL FUNDING NOTICE

This invention was made with government support under Federal Grant Nos. DK098503, CA208236, and EB011527 awarded by the National Institutes of Health. The Government has certain rights in the invention.

BACKGROUND

Prostate cancer (PCa) is a common cancer in men and may cause over 25,000 deaths in the United States alone in 2015. Conventionally, prostate cancer has been diagnosed using a multi-step approach. For example, a biopsy may be performed after a test that revealed worrisome levels of a prostate specific antigen (PSA). In some cases, invasive biopsies may be obtained without a priori knowledge of the location or existence of focal lesions identified on imaging. The biopsy may be performed by transrectal ultrasound (TRUS) guidance, blind to the cancerous lesion or with various forms of targeting with an MRI, and may involve sampling regions of the gland. These multiple steps may have required multiple visits to the hospital over an extended period of time, during which the patient may have been anxious or otherwise inconvenienced. Even after all the steps were taken, a diagnosis may still have been a subjective thing based on how a doctor interpreted the results of the tests for any specific patient. Interpretation may have been subjective with different doctors arriving at different diagnoses. Additionally, excessive biopsy and treatment of low grade PCa may cause more harm than good.

Magnetic resonance (MR) techniques have been employed to attempt to differentiate normal tissue from PCa. For example, conventional T2 weighted images, diffusion weighted images (DWI) with apparent diffusion coefficient (ADC) mapping, dynamic contrast-enhanced MRI (DCE-MRI), and MR spectroscopy (MRS) have been evaluated for differentiating normal tissue from PCa. The ability to use these conventional tools may have been limited by the qualitative nature of the images and the resulting subjective analysis.

When MR images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration. Different viewers may arrive at different diagnoses when reading the same images.

Characterizing tissue species using nuclear magnetic resonance (NMR) can include quantifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using magnetic resonance fingerprinting (MRF), which is described in *Magnetic Resonance Fingerprinting*, Ma D et al., Nature 2013:495, (7440): 187-192. MRF has not previously been applied to identifying or grading PCa.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example apparatus and methods provide a quantitative nuclear magnetic resonance (NMR) exam for assessing prostate cancer (PCa). Example apparatus and methods combine quantitative magnetic resonance fingerprinting (MRF) based T1 and T2 mapping with quantitative magnetic resonance imaging (MRI) based apparent diffusion coefficient (ADC) mapping to identify and grade prostrate tumors. The quantitative NMR exam is based on differences between parameters including T1, T2, ADC, and perfusion in PCa tissue and normal tissue (e.g., normal peripheral zone (NPZ) tissue). MRF generated T1 and T2 parameters are combined with ADC mapping and/or quantitative perfusion values to generate a multi-property quantitative space (e.g., two, three, or four property quantitative space) for characterizing prostate cancer, prostatitis, and normal prostate tissue. The results illustrated in FIGS. 1-5 demonstrate that MRF-derived relaxometry may be used to quantitatively differentiate PCa from NPZ.

Figure 1:
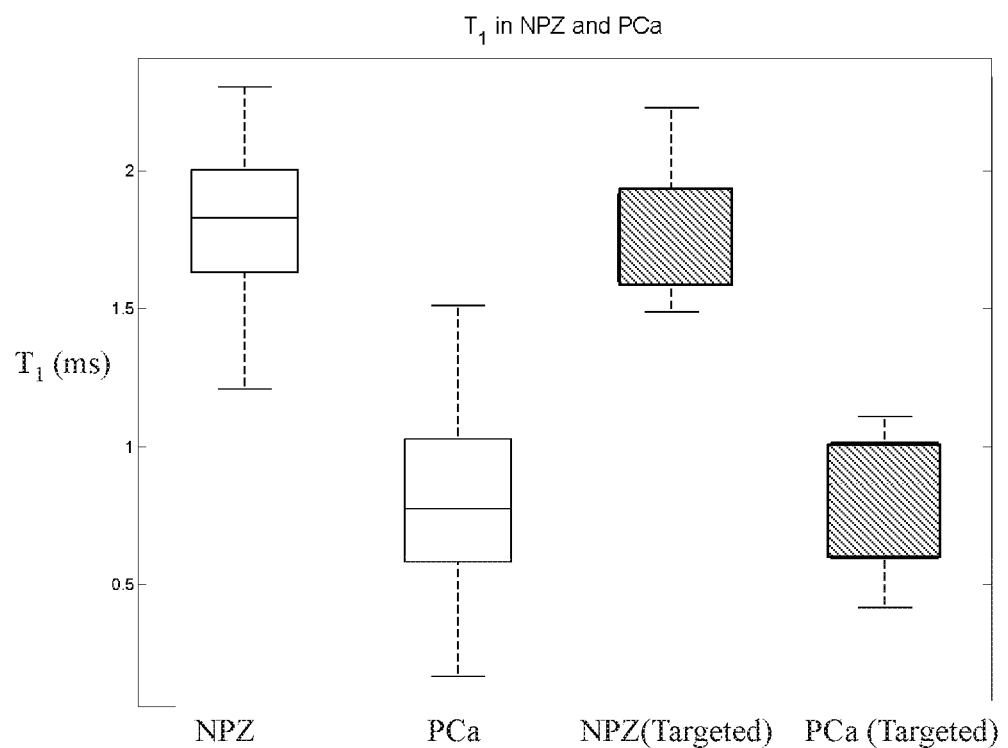
FIG. 1 illustrates T1 in normal peripheral zone (NPZ) tissue and prostate cancer (PCa) tissue.

FIG. 1 illustrates T1 in NPZ and PCa. T1 is longer in NPZ and shorter in PCa. Since the T1 values for PCa and NPZ vary within different ranges, they may provide a clue for separating NPZ from PCa.

Figure 2:
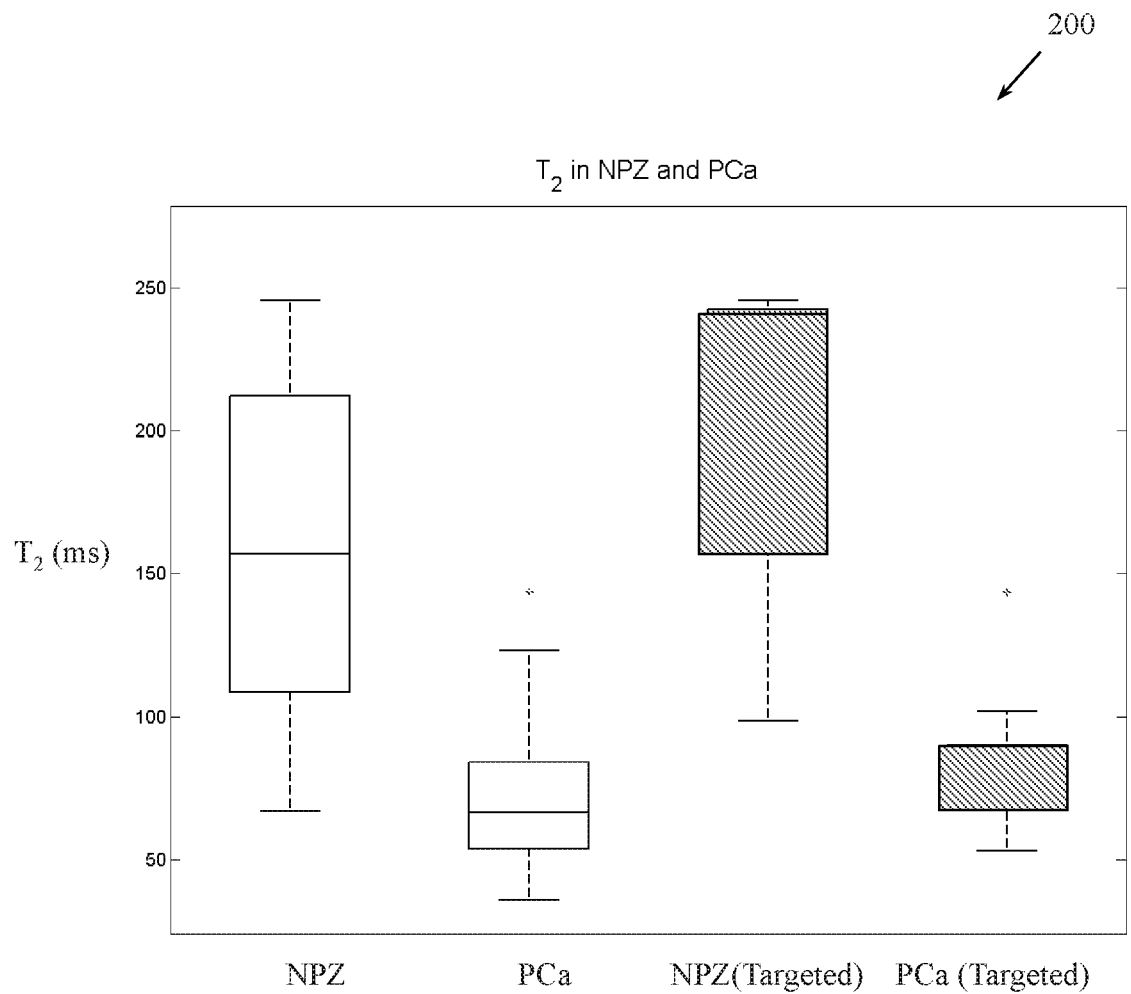
FIG. 2 illustrates T2 in NPZ and PCa.

FIG. 2 illustrates T2 in NPZ and PCa. T2 is longer in NPZ and shorter in PCa. Since the T2 values for PCa and NPZ vary within different ranges, they may also provide a clue for separating NPZ from PCa.

Figure 3:
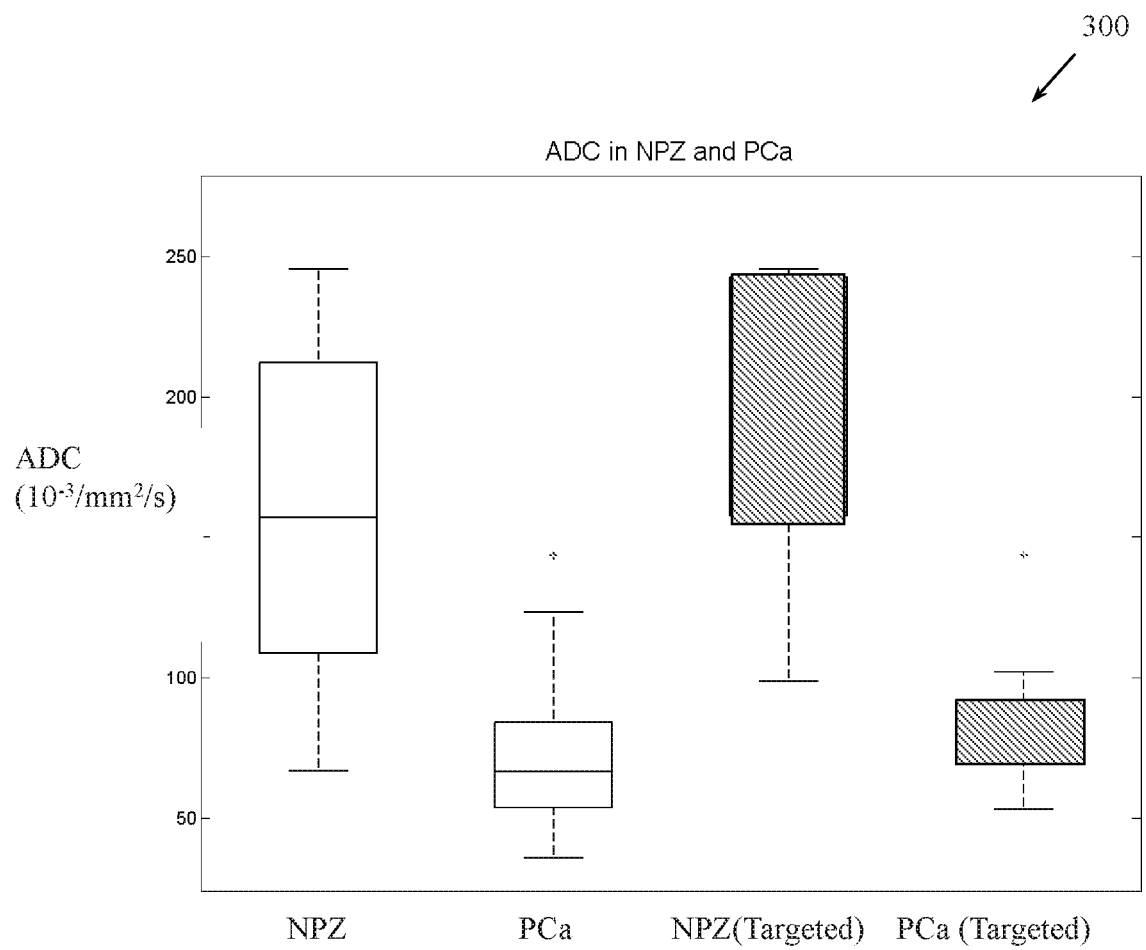
FIG. 3 illustrates apparent diffusion co-efficient (ADC) in NPZ and PCa.

FIG. 3 illustrates ADC in NPZ and PCa. ADC is greater in NPZ and lesser in PCa. Since the ADC values for PCa and NPZ vary within different ranges, they may be provide another clue for separating NPZ from PCa. While the individual values for T1, T2, and ADC may provide clues for separating NPZ from PCa, weighted combinations of the values may provide superior clues.

Figure 4:
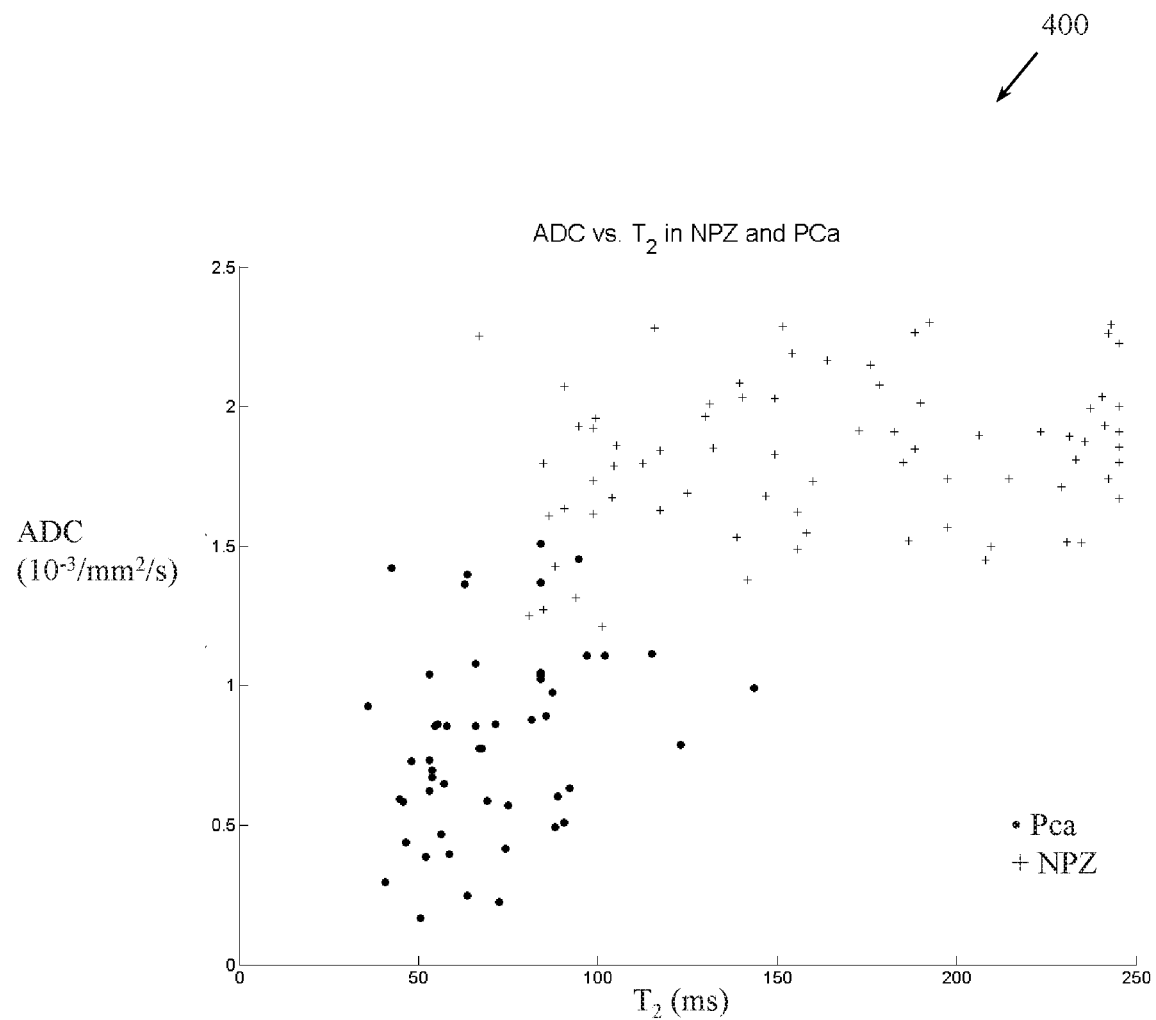
FIG. 4 illustrates ADC vs T2 in NPZ and PCa.

FIG. 4 illustrates ADC vs T2 in NPZ and PCa. Data points associated with PCA are grouped in the lower left of FIG. 4 and data points associated with NPZ are grouped in the top center and top right of FIG. 4. The combination of ADC and T2 may provide a superior clue for separating PCa from NPZ.

Figure 5:
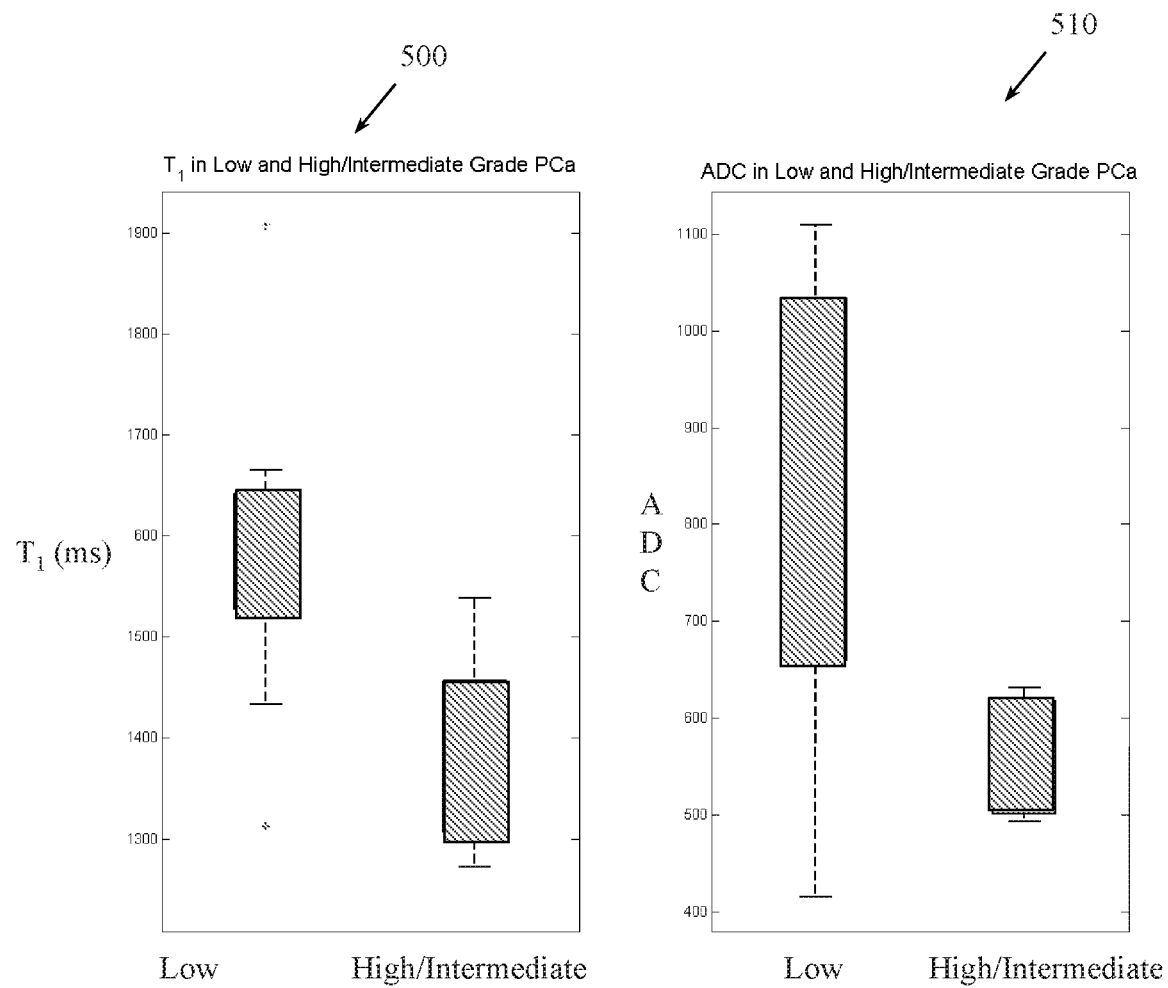
FIG. 5 illustrates T1 and ADC in low and high/intermediate grade PCa.

FIG. 5 illustrates T1 in low and high/intermediate grade PCa and ADC in low and high/intermediate grade PCa. T1 is longer in low grade PCa and is shorter in high/intermediate grade PCa. Here, a high grade tumor is defined as a tumor whose Gleason score is greater than 4+4=8. An intermediate grade tumor is defined a tumor whose Gleason score is 3+4=7 or 4+3=7. A low grade tumor is a tumor whose Gleason score is 3+3=6.

FIGS. 1-5 demonstrate that when quantitative values for T1, T2, and ADC are available, a quantitative NMR exam can non-invasively identify and assess prostate cancer based, at least in part, on a weighted combination of the quantitative values. Thus, example apparatus and methods employ MRF-based quantitative T1 and T2 mapping for clinical characterization of pathology. In one embodiment, quantitative MRF based T1 and T2 mapping may be combined with quantitative MRI based ADC mapping and/or quantitative MRI based perfusion mapping to non-invasively identify and grade prostate tumors. In one embodiment, quantitative T1 and T2 mapping may be performed simultaneously with quantitative ADC mapping. In one embodiment, an MRF based fast imaging with steady state precision (FISP) pulse sequence may be applied to portions of the prostate gland in a volumetric multi-slice acquisition. The MRF-FISP pulse sequence may be applied before contrast agent administration. Quantitative T1 and T2 parameter maps may be generated and analyzed in light of quantitative ADC maps.

MRF plus diffusion can quantitatively differentiate PCa from NPZ. A two-property space of ADC and MRF derived T2 provides separation of PCa from NPZ with AUC of 0.993. A three-property space of MRF derived T1 and T2 with clinical ADC provides separation between high/intermediate grade PCa and low-grade PCa with AUC of 0.882.

Identifying and grading PCa is possible because T1, T2, and ADC from PCa are lower than T1, T2 and ADC from NPZ. While individual quantitative values may provide some diagnostic ability, a weighted combination of quantitative values may provide a greater diagnostic ability. For example, a combination of quantitative T2 values and ADC values may produce a superior separation between PCa and normal tissues. In another example, a combination of quantitative T1 values, quantitative T2 values, and ADC values may produce a superior separation between high/intermediate, and low grade cancer tumors.

MRF provides a new paradigm for MRI acquisition and reconstruction. MRF also provides new opportunities for quantitative analysis of acquired data. MRF facilitates rapid, efficient, and simultaneous quantification of multiple tissue properties. MRF generates quantitative maps of interesting tissue properties using sparse time variant MR data matched against a collection of possible signal time courses. The signal time courses may be constructed from, for example, the Bloch equations. Properties like T1 and T2 may be intrinsic to tissue types and thus may differ in statistically significant ways between tissue types. Thus, T1 and T2 may provide information that allows non-invasive tissue characterization that is more accurate than previously thought feasible.

Example apparatus and methods use MRF for accurate and high-resolution quantification of multiple tissue properties in the prostate. In one embodiment, example apparatus and methods may facilitate classifying a tissue as being PCa tissue or NPZ tissue. Example apparatus and methods employ MRF to acquire T1 and/or T2 relaxometry values for tissues to be classified. Example apparatus and methods also employ MRI to acquire ADC values from which a quantitative diffusion map may be generated. Example apparatus and methods may also employ dynamic contrast enhanced (DCE)-MRI to acquire quantitative perfusion data. The quantitative perfusion data may include, for example, $K^{Trans}$, $K_{ep}$, and $V_e$, where $K^{Trans}$ is the volume transfer constant, $V_e$ is the fractional volume, and $K_{ep}=K^{Trans}/V_e$.

While MRF alone provides an extremely useful tool, MRF in combination with DWI-MRI and/or DCE-MRI may provide an even more superior tool for identifying and grading prostate tumors. For example, when MRF T2 measurements are combined with MRI ADC measurements, complete separation of PCa and NPZ may be achieved.

ADC refers to apparent diffusion coefficient (ADC), which is the measure of the magnitude of diffusion of water molecules in tissue. ADC is clinically calculated using MRI with diffusion weighted imaging (DWI). DWI exploits the random motion of water molecules. The freedom of water molecules to diffuse within a water medium can be quantitatively assessed using the ADC value. The diffusivity may be affected by properties including the extent of tissue cellularity and the presence of intact cell membranes. The ADC value may be assessed using, for example different b values via changing gradient amplitudes. ADC values may be displayed as a parametric map that reflects the degree of diffusion of water molecules through different tissues. Ca tissue and NPZ tissue may exhibit different ADC.

The ADC is expressed in units of $mm^2/s$. Some example ADC values ($\times 10^{-6}$ $mm^2/s$) include:
  white matter: 670-800
  cortical grey matter: 800-1000
  deep grey matter: 700-850
  CSF: 3000-3400
  Astrocytoma Gd II: 1273±293
  Astrocytoma Gd III: 1067±276
  Astrocytoma Gd IV: 745±135
  Example apparatus and methods may acquire multiple two dimensional (2D) slices through the prostate using MRF-FISP with randomized repetition times and flip angles. The multiple 2D slices may be transverse slices.

In one embodiment, imaging parameters may be FOV 40×40 cm, in-plane spatial resolution 1×1 mm$^2$, matrix size 256×256, slice thickness 5 mm, variable repetition time (TR) from 11-15 ms, and variable flip angles (FA) from 5-75 degrees. In one embodiment, under-sampled images may be acquired in less than 30 seconds. In one embodiment, up to 50s per slice acquisition may be employed. The entire volume of the gland may be covered without gaps using 6-12 slices. Other numbers of images may be acquired in different periods of time using different imaging parameters.

To facilitate producing quantitative values for tissue properties (e.g., T1, T2) in response to NMR signals produced during MRF-FISP of the prostate, a dictionary including signal evolutions from combinations of parameters for a T1 range of 20 ms to 3000 ms and a T2 range of 9 ms to 245 ms may be calculated using Bloch simulations. The acquired signal in different pixels of the images produced using MRF-FISP of the prostrate may be matched to an entry from this dictionary. The matching may be performed using orthogonal matching pursuit (OMP). While OMP is described, other matching approaches may be employed. The matching may yield underlying parameters that were used to form the dictionary entry.

Experiments using example apparatus and methods were verified using MRF data collected from volunteers that presented with different conditions including PCa as shown by biopsy proven lesions, diffusely infiltrative disease, measurable NPZ, scar tissue from previous biopsy, or other conditions. T1 and T2 maps were generated from NMR signals acquired using MRF-FISP. Region of interest (ROI) evaluation was performed for the target lesion(s) and NPZ. ROI analysis was also performed on corresponding clinical ADC maps. Student's t-test was used to differentiate between PCa and NPZ based on T1, T2, and ADC values.

In one set of data produced from one set of patients, PCa and NPZ produced different measurements as described in table 1.

TABLE 1

|  | PCa | NPZ |
|---|---|---|
| T1 | 1129 ms ± 293 ms | 1387 ms ± 173 ms |
| T2 | 68 ms ± 12 ms | 130 ms ± 40 ms |
| ADC | 390 ± 203 × 10$^{-6}$ mm$^2$/s | 1572 ± 155 × 10$^{-6}$ mm$^2$/s |

In this set of data, the values for PCa and NPZ differ as described in the table below:

|  | PCa vs. NPZ |
|---|---|
| T1 | p < 0.02 |
| T2 | p < 0.003 |
| ADC | p < 10$^{-7}$ |

In another set of data produced from another set of patients, PCa and NPZ produced different measurements as described in table 2.

|  | PCa | NPZ |
|---|---|---|
| T1 | 1517 ms ± 293 ms | 2181 ms ± 173 ms |
| T2 | 70 ms ± 12 ms | 166 ms ± 40 ms |
| ADC | 805 ± 203 × 10$^{-6}$ mm$^2$/s | 1794 ± 155 × 10$^{-6}$ mm$^2$/s |

In another set of data from another set of patients, mean (±sd) values for T1, T2, and ADC for PCa were 1503±348 ms, 71±22 ms, and 788±329×10$^{-6}$ mm$^2$/s, respectively. For NPZ these values were 2147±523 ms, 163±56 ms, and 1815±267×10$^{-6}$ mm$^2$/s, respectively. Although ranges and values may vary for different data sets, the relationships between T1, T2, and ADC values for PCa for NPZ are consistent. T1, T2, and ADC are all lower for PCA than for NPZ.

T1, T2, and ADC values in high and intermediate grade tumors were compared to those seen in low grade disease. One example data set included 37 low grade, 8 intermediate grade, and 12 high grade tumors. Mean T1, T2 and ADC values for each grading group are displayed in Table 2.

TABLE 2

| Histology | N | T1 (ms) Mean | T1 (ms) SD | T2 (ms) Mean | T2 (ms) SD | ADC (×10$^{-3}$ mm$^2$/s) Mean | ADC (×10$^{-3}$ mm$^2$/s) SD |
|---|---|---|---|---|---|---|---|
| NPZ | 86 | 2148 | 523 | 163 | 56 | 1.815 | 0.267 |
|  | 23 | 2360 | 489 | 196 | 49 | 1.790 | 0.205 |
| Peripheral zone PCa | 57 | 1503 | 348 | 71 | 22 | 0.788 | 0.329 |
|  | 15 | 1539 | 168 | 84 | 21 | 0.775 | 0.237 |
| Low grade | 37 | 1576 | 318 | 75 | 23 | 0.896 | 0.298 |
|  | 11 | 1585 | 150 | 82 | 24 | 0.854 | 0.228 |
| Intermediate grade | 8 | 1478 | 255 | 59 | 14 | 0.662 | 0.325 |
|  | 1 | 1272 | — | 89 | — | 0.602 | — |
| High grade | 12 | 1278 | 423 | 66 | 20 | 0.536 | 0.267 |
|  | 3 | 1419 | 104 | 90 | 2 | 0.545 | 0.76 |

| Comparison | Statistic | T1 | T2 | ADC | Highest AUC |
|---|---|---|---|---|---|
| NPZ v. PCa | p-value* | <0.0001 | <0.0001 | <0.0001 | ADC + T2 combined |
|  | AUC | 0.850 | 0.953 | 0.991 | (AUC = 0.994) |
|  | (p-value)** | (<0.0001) | (<0.0001) | (<0.0001) |  |
| High/intermediate v. Low grade | p-value | 0.12 | 0.85 | 0.012 | ADC only |
|  | AUC | 0.681 | 0.649 | 0.786 | (AUC = 0.786) |
|  | (p-value)** | (0.059) | (0.072) | (0.0041) |  |

*Based on linear mixed model
**Based on GEE logistic regression

High and intermediate grade tumors were grouped because of similar treatment and prognosis. By linear mixed model, ADC differed significantly (p=0.048) between grouped high and intermediate grade lesions compared to low grade. By generalized estimating equations (GEE) logistic regression, ADC showed significant separation of high and intermediate grades from low grade with area under curve (AUC) of 0.79 (p=0.0041). Separation by T1 neared significance as a univariable model with an AUC of 0.68 (p=0.059). In this dataset, as illustrated in table 3, T1 and ADC demonstrated significant discrimination of grouped high and intermediate grades from low grade cancers.

TABLE 3

| Histology | N | T1 (ms) Mean | T1 (ms) SD | T2 (ms) Mean | T2 (ms) SD | ADC ($\times 10^{-3}$ mm²/s) Mean | ADC ($\times 10^{-3}$ mm²/s) SD |
|---|---|---|---|---|---|---|---|
| NPZ | 23 | 2360 | 489 | 196 | 49 | 1.790 | 0.205 |
| Peripheral zone PCa | 15 | 1539 | 168 | 84 | 21 | 0.775 | 0.237 |
| Low grade | 11 | 1585 | 150 | 82 | 24 | 0.854 | 0.228 |
| Intermediate grade | 1 | 1272 | — | 89 | — | 0.602 | — |
| High grade | 3 | 1419 | 104 | 90 | 2 | 0.545 | 0.76 |

| Comparison | Statistic | T1 | T2 | ADC | Highest AUC |
|---|---|---|---|---|---|
| NPZ v. PCa | p-value* | <0.0001 | <0.0001 | <0.0001 | ADC only |
|  | AUC (p-value)** | 0.968 (0.006) | 0.986 (0.001) | 1.0 *** | (AUC = 1.0***) |
| High/intermediate v. Low grade | p-value | 0.018 | 0.60 | 0.029 | T1 only |
|  | AUC (p-value)** | 0.886± | 0.818± | 0.841± | (AUC = 886±) |

*Based on linear mixed model
**Based on GEE logistic regression

Example apparatus and methods revealed differences between patients having had a recent biopsy (e.g., in previous 16 months) as compared to patients having had a more remote biopsy (e.g., outside previous 16 months) or patients who had not had a biopsy. Patients with a more recent biopsy produced lower T1 values in their NPZ (p<0.005) as compared to patients who had a more remote or no biopsy. A linear increase in T1 of NPZ appears over time after biopsy. The linear relationship may hold for up to five years after biopsy. The linear relationship may be related to hemorrhagic products, scar tissue, or other biopsy related trauma.

Although the exact mechanisms may not be completely agreed upon, T2 shortening has been attributed to decreased citrate concentration in prostate malignancy secondary to loss of zinc-accumulating ability of the neoplastic cells. The drop in ADC has been hypothesized to relate to the decrease in diffusion that results from increased cellular density occurring in cancerous tissue. Regardless of the mechanisms, the observed results suffice for separating PCa from NPZ using quantitative values from MRF-based T1 and T2 mapping and MRI-based ADC mapping.

In MRF, pseudorandom signal evolutions may be compared to a dictionary of stored signal evolutions. The comparison may be performed using, for example, an OMP technique. (See, e.g., Doneva M, et al. MRM, 2010) The stored signal evolutions may be from previous acquisitions or may even be from theoretical models. For example, the stored signal evolutions can be from a set described by:

$$SE = \sum_{i=1}^{N_S} \prod_{i=1}^{N_A} \sum_{j=1}^{N_{RF}} R_{i(\alpha)} R_{RF_{ij}(\alpha,\phi)} R(G) E_i(T1, T2, \ldots) DPdM_0 \quad [1]$$

or $$SE = \sum_{i=1}^{N_S} \prod_{i=1}^{N_A} \prod_{j=1}^{N_{RF}} R_i(\alpha) R_{RF_{ij}(\alpha,\phi)} R(G) E_i(T1, T2, \ldots) DPdM_0 \quad [2]$$

where:

SE is a signal evolution, $N_S$ is a number of spins, $N_A$ is a number of sequence blocks, $N_{RF}$ is a number of RF pulses in a sequence block, a is a flip angle, φ is a phase angle, Ri(α) is a rotation due to off resonance, $R_{RFij}(\alpha,\phi)$ is a rotation due to RF differences, R(G) is a rotation due to a gradient, T1 is spin-lattice relaxation, T2 is spin-spin relaxation, D is diffusion relaxation, Pd is proton density, $E_i$(T1, T2, ... ) is decay due to relaxation differences, and $M_0$ is the default or equilibrium magnetization.

Some MRF investigations may involve a sample for which there is a priori knowledge about the resonant species that are likely to be encountered. The a priori knowledge may even include information concerning possible or expected ratios of the amounts of the resonant species or resonant tissues to be encountered in the sample. When the sample has some properties (e.g., T1 relaxation time, T2 relaxation time) that are likely to fall in a certain range, then it may be possible to simplify or even focus the pattern matching portion of MRF.

MRF involves measuring pseudorandom MR signal evolutions produced in response to MRF pulse sequences. MRF also includes generating modeled signal evolutions that may be stored in a dictionary. The dictionary entries may be a function of several parameters. If the composition of the sample to be interrogated is known ahead of time, then a mathematical operation (e.g., weighted sum) of dictionary entries corresponding to the known components may be used to model signal evolutions and an inverse mathematical operation (e.g., matrix pseudo-inverse) may be used to compute the relative fraction of components assumed to be present based on a received signal evolution.

Data from additional studies performed on a different set of patients is presented in tables four and five.

TABLE 4

| Histology | N | T1 (ms) Mean | SD | T2 (ms) Mean | SD | ADC ($\times 10^{-3}$ mm$^2$/s) Mean | SD |
|---|---|---|---|---|---|---|---|
| NPZ | 79 | 2181 | 509 | 166 | 52 | 1.794 | 0.258 |
| Peripheral zone PCa | 49 | 1517 | 324 | 70 | 20 | 0.805 | 0.342 |
| Low grade | 14 | 1539 | 336 | 84 | 20 | 1.065 | 0.324 |
| Intermediate grade | 25 | 1593 | 217 | 64 | 17 | 0.759 | .272 |
| High grade | 10 | 1297 | 448 | 65 | 22 | 0.545 | 0.282 |
| Prostatitis | 18 | 1616 | 392 | 79 | 35 | .924 | .250 |

TABLE 5

| Comparison [N] | T1 | T2 | ADC | Highest AUC |
|---|---|---|---|---|
| PCa [49] vs. NPZ [79] | 0.865 | 0.968 | 0.986 | 0.993 |
| High [10] vs. Low [39] | 0.531 | 0.772 | 0.807 | 0.882 |
| PCa [49] vs. Prostatitis [18] | 0.519 | 0.570 | 0.622 | 0.622 |
| Prostatis [18] vs. NPZ [79] | 0.804 | 0.913 | 0.992 | 0.992 |

T1, T2, and ADC from PCa were significantly lower than NPZ. T2 and ADC together produced near complete separation between PCa and NPZ. T1, T2, and ADC separated between intermediate/high grade tumors and low-grade tumors. T1, T2 and ADC from prostatitis were significantly different from NPZ.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to one embodiment", an embodiment", one example", an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a non-transitory medium that stores signals, instructions and/or data. "Computer-readable storage medium" does not refer to propagated signals. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

"Logic", as used herein, includes but is not limited to hardware and firmware and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, or other circuit elements. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"User", as used herein, includes but is not limited to one or more persons, software, computers or other devices, or combinations of these.

Figure 6:
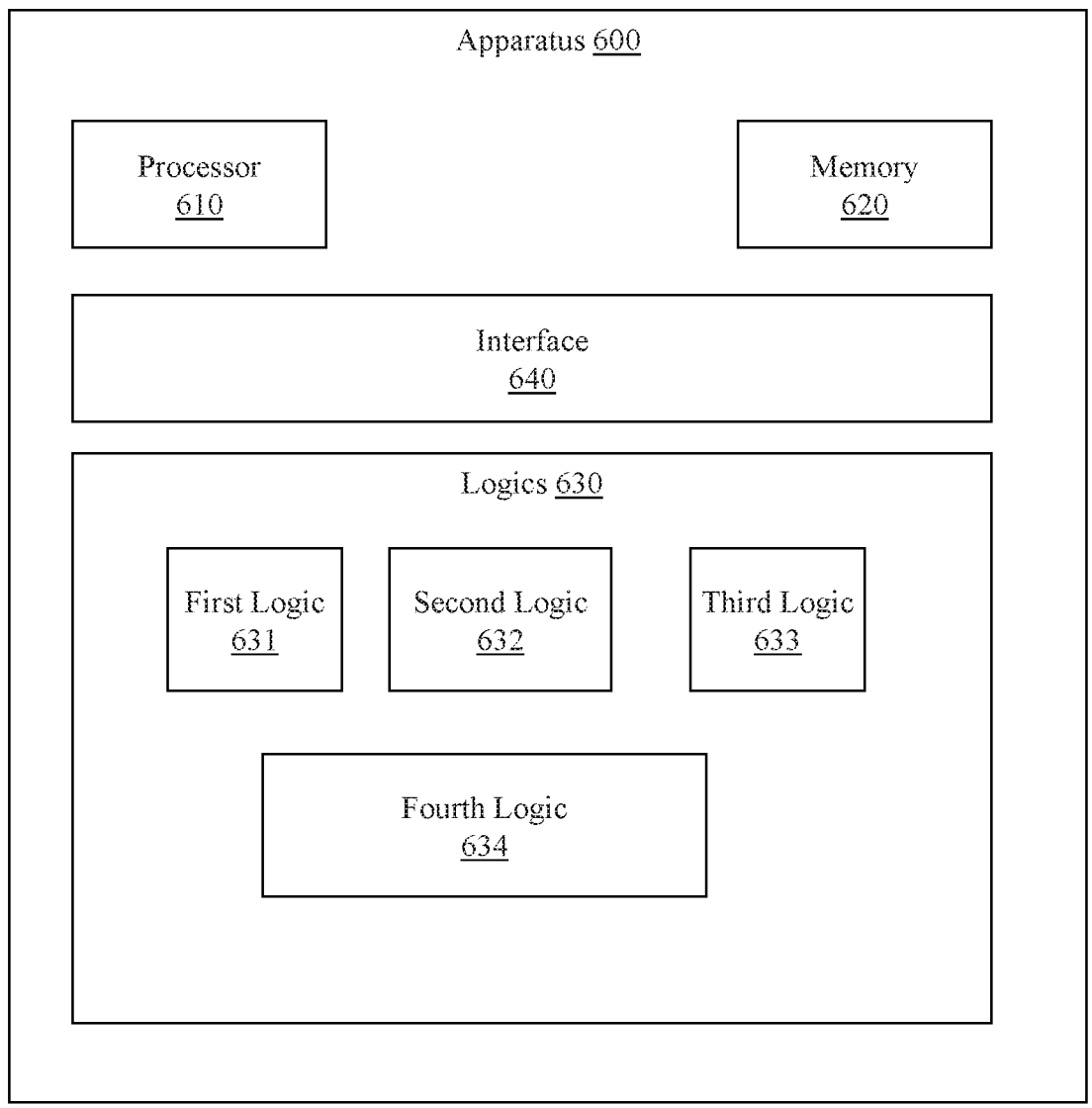
FIG. 6 illustrates an example MR apparatus associated with quantitative prostate cancer imaging using magnetic resonance fingerprinting (MRF) in combination with another magnetic resonance imaging (MRI) technique(s).

FIG. 6 illustrates an apparatus 600 that includes a processor 610, a memory 620, a set of logics 630, and a hardware interface 640 that connects the processor 610, the memory 620, and the set of logics 630.

The set of logics 630 includes a first logic 631 that controls the processor 610 to produce a first quantitative parametric map of a portion of a human prostate. The first quantitative parametric map is associated with a first NMR property of one or more tissues in the portion. In one embodiment the first quantitative parametric map may be displayed.

The set of logics 630 also includes a second logic 632 that controls the processor 610 to produce a second quantitative parametric map of the portion. The second quantitative parametric map is associated with a second NMR property of one or more tissues in the portion. In one embodiment the second quantitative parametric map may be displayed.

In different examples, the first quantitative parametric map and the second quantitative parametric maps may hold different types of information. In one embodiment, the first quantitative parametric map is a T1 map or a T2 map, and the second quantitative parametric map is a diffusion map produced from data acquired using DWI-MRI. In another embodiment, the first quantitative parametric map is a T1 map or a T2 map, and the second quantitative parametric map is a perfusion map produced from data acquired using DCE-MRI. The quantitative values for the T1 map and quantitative values for the T2 map may be acquired in response to an MRF-FISP pulse sequence. In one embodiment, the MRF-FISP pulse sequence is used in an MRF scan that acquires multiple transverse 2D slices of the portion. In one embodiment, TR in the MRF-FISP pulse sequence may vary from 11-13 ms and FA may vary from 5-75 degrees. Different ranges of TR and FA may be employed.

The set of logics 630 also includes a third logic 633 that controls the processor 610 to produce a quantitative multi-parametric map from the first quantitative parametric map and the second quantitative parametric map. Entries in the quantitative multi-parametric map may be a weighted combination of entries from the first quantitative parametric map and the second quantitative parametric map. In one embodiment, the weights for one parametric map may be zero. The third logic 633 may display the multi-parametric map.

The set of logics 630 also includes a fourth logic 634 that controls the processor 610 to produce an output that separates prostate cancer tissue from non-cancerous tissue in the portion based on the quantitative multi-parametric map. In one embodiment, the fourth logic 634 controls the processor 610 to grade the prostate cancer tissue based on the quantitative multi-parametric map. The fourth logic 634 may display an image that illustrates regions having prostate cancer tissue and regions not having prostate cancer tissue. The image may be a modification of the multi-parametric map.

Figure 7:
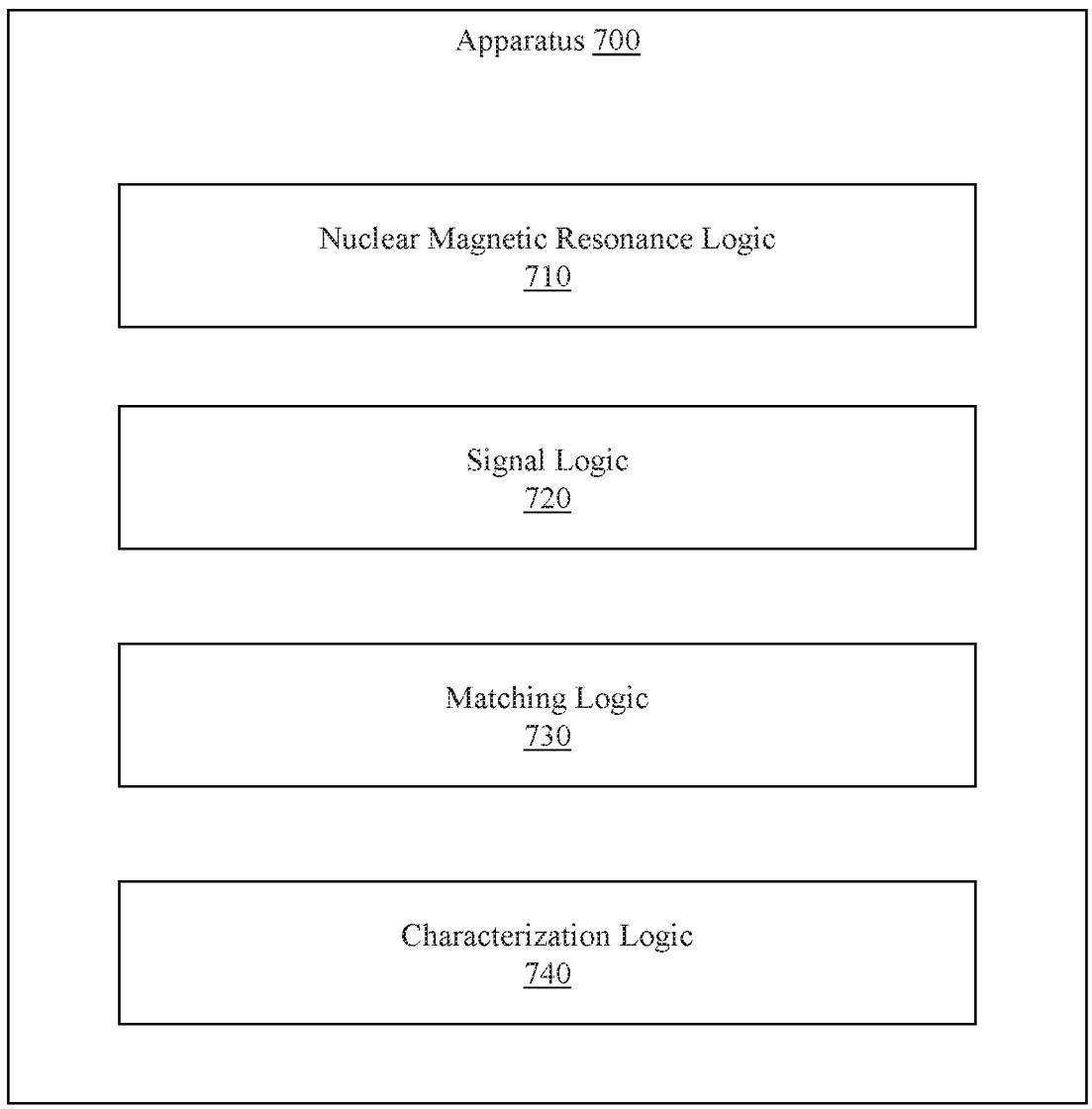
FIG. 7 illustrates an example MR apparatus associated with quantitative prostate cancer imaging using MRF and another MRI technique(s).

FIG. 7 illustrates an MRF apparatus 700. MRF apparatus 700 may, for example, be part of a Siemens 3T Skyra scanner having 32 receive channels. MRF apparatus 700 may simultaneously quantify MR parameters including T1 and T2 for an object (e.g., prostate) to which an MRF pulse sequence is applied.

MRF apparatus 700 includes an NMR logic 710 that receives a first set of data from an MRF apparatus that repetitively and variably samples a (k, t, E) space associated with a human prostate to acquire a set of NMR signals. The MRF apparatus applies RF energy to the prostate according to an MRF pulse sequence to cause the prostate to produce the set of NMR signals. The MRF pulse sequence may be an MRF-FISP sequence. Members of the first set of data are associated with different points in the (k, t, E) space, where t is time and E includes at least T1 or T2, T1 being spin-lattice relaxation and T2 being spin-spin relaxation. At least one of t and E vary non-linearly.

MRF apparatus 700 also includes a signal logic 720 that produces an NMR signal evolution from the first set of data.

MRF apparatus 700 also includes a matching logic 730 that selects, from a collection of stored signal evolutions, a selected stored signal evolution that matches the NMR signal evolution to within a desired tolerance. The matching logic 730 retrieves quantitative information about the human prostate using the selected stored signal evolution. "Match" as used herein refers to the result of comparing signals. "Match" does not refer to an exact match, which may or may not be found. A match may be the signal that most closely resembles another signal. A match may be the first signal that matches another signal to within a threshold. A match may be found by template matching, pattern matching, or other comparison approaches. The reference information may be, for example, a previously acquired signal evolution, a simulated signal evolution, an item derived from a signal evolution other than the produced NMR signal evolution, and other information. The reference information may include signal evolutions from different tissue types (e.g., healthy, diseased, advanced disease, normal, abnormal). The reference information may include signal evolutions that are formed from combinations of resonant species with combinations of MR parameters.

In one embodiment, the collection of stored signal evolutions includes a signal evolution having information associated with a first resonant species and a second resonant species. The information associated with the first resonant species may be produced by controlling an MR property or properties associated with the first resonant species to be constant or to be within a first known range or ranges. Information associated with the second resonant species may also be produced by controlling an MR property or properties associated with the second resonant species to be constant or to be within a second known range or ranges. When the collection of stored signal evolutions includes signal evolutions associated with a finite, small (e.g., 2, 3) number of resonant species, and when the signals used to produce the signal evolutions are constrained within well-defined ranges, then relative fractions of the resonant species that contributed to the acquired NMR signal evolution may be determined from the matched signal evolution. The relative fractions may be determined in different ways. In one example, the relative fractions may be decoded from the matched signal evolution.

In one embodiment, the information concerning the first resonant species may be combined with the information concerning the second resonant species using a weighted sum operation. When the weighted sum approach is employed, then information concerning relative proportions of resonant species that contributed to the selected stored signal evolution may be retrievable from the selected stored signal evolution in response to performing a matrix pseudo-inverse operation on the selected stored signal evolution.

More generally, the collection of stored signal evolutions include a signal selected from equations [1] or [2] described above.

In one embodiment, the collection of stored signal evolutions include a signal selected from:

$$S_i = R_i E_i (S_{i-1}) \qquad [3]$$

or $$S_i = R_i E_i \sum_{x=1}^{i-1} R_x E_x (S_x) \qquad [4]$$

or $$S_i = R_i E_i \prod_{x=1}^{i-1} R_x E_x (S_x) \qquad [5]$$

or $$S_i = \sum_{s=1}^{N_s} R_{s,i} E_{s,i} (S_{s,i-1}) \qquad [6]$$

or $$S_i = \sum_{s=1}^{N_s} R_{s,i} E_{s,i} \sum_{x=1}^{i-1} R_{s,x} E_{s,x} (S_{s,x}) \qquad [7]$$

or $$S_i = \sum_{s=1}^{N_s} R_{s,i} E_{s,i} \prod_{x=1}^{i-1} R_{s,x} E_{s,x} (S_{s,x}) \qquad [8]$$

where:

$S_0$ is the default or equilibrium magnetization, $S_i$ is a vector that represents the different components of the magnetization Mx, My, Mz during acquisition block i, $R_i$ is the combination of rotational effects that occur during acquisition block i, and $E_i$ is the combination of effects that alter the amount of magnetization in the different states for acquisition block i. Equations 1-8 may be referred to collectively as the MRF dictionary equations.

Apparatus 700 also includes a characterization logic 740 that identifies the prostate as having a first property based, at least in part, on the quantitative information. The first property describes whether the prostate has resonant species exhibiting attributes that fall within a first specified range that indicates the prostate includes cancer tissue. In one embodiment, the first specified range is T1 in the range 1129 ms±293 ms and T2 in the range 68 ms±12 ms.

In one embodiment, the NMR logic 710 receives a second set of data from an MRI apparatus that performs a DWI-MRI acquisition from the prostate. In this embodiment, the characterization logic 740 updates the quantitative information with elements of the second set of data. The characterization logic 740 then identifies the prostate as having a second property based, at least in part, on the updated quantitative information. The second property describes whether the prostate has resonant species exhibiting attributes that fall within a second specified range that indicates the prostate includes cancer tissue. In one embodiment, the second specified range is T1 in the range 1129 ms±293 ms, T2 in the range 68 ms±12 ms, and ADC in the range $390\pm203\times10^{-6}$ $mm^2/s$.

Figure 8:
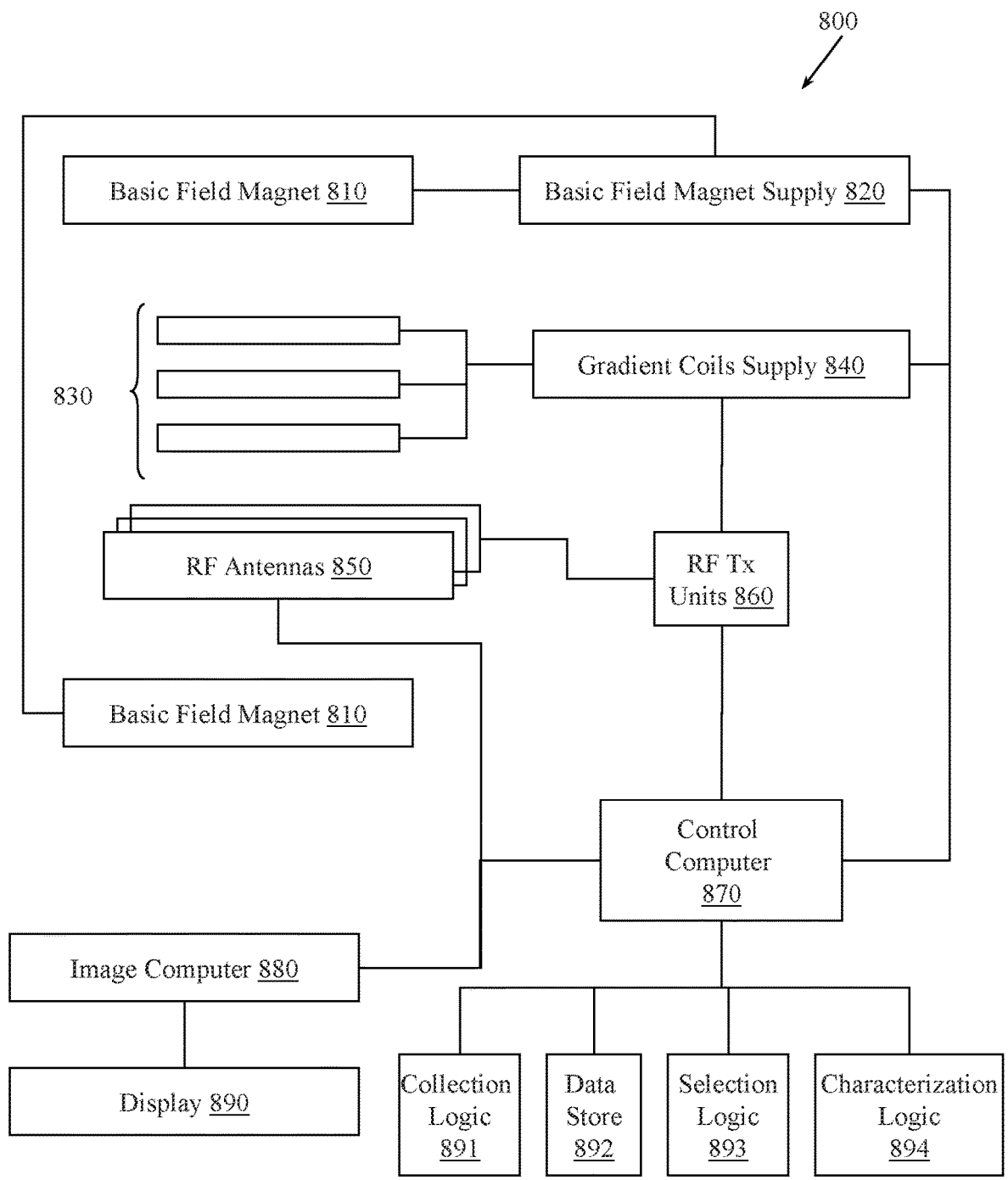
FIG. 8 illustrates an example MR apparatus associated with quantitative prostate cancer imaging using MRF and another MRI technique(s).

FIG. 8 illustrates an example MR apparatus 800 having a collection logic 891, a data store 892, a selection logic 893, and a characterization logic 894 that facilitate identifying PCa tissue. The identifying may be based, at least in part, on T1 values, T2 values, ADC values, or other values (e.g., perfusion). The collection logic 891, data store 892, selection logic 893, and characterization logic 894 may be configured with elements of example apparatus described herein or may perform example methods described herein. While collection logic 891, data store 892, selection logic 893, and characterization logic 894 are illustrated as part of MR apparatus 800, in one example, collection logic 891, data store 892, selection logic 893, and characterization logic 894 may be separate apparatus.

In one embodiment, collection logic 891 collects a received signal evolution from tissue in a prostate experiencing NMR in response to an MRF-FISP excitation applied to the tissue by the MRI apparatus 800. Data store 892 may store a dictionary of MRF signal evolutions. Members of the dictionary are combinations of information associated with a resonant species associated with prostate cancer. Information concerning the composition of the tissue with respect to the resonant species is retrievable using a matched signal evolution. Selection logic 893 selects a matching member of the dictionary that is most closely related to the signal evolution and establishes the matching member as the matched signal evolution. Characterization logic 894 identifies whether the prostate includes the resonant species associated with prostate cancer based, at least in part, on the matched signal evolution.

In one embodiment, the characterization logic 894 identifies whether the prostate include the resonant species associated with PCa using a quantitative magnetic resonance based approach. For example, the characterization logic 894 may identify that the prostate includes the resonant species associated with PCa upon identifying that the tissue has T1 in the range 1129 ms±293 ms or T2 in the range 68 ms±12 ms.

In one embodiment, the collection logic 891 collects a second NMR signal from the tissue in response to a DWI-MRI acquisition. The collection logic 891 produces a quantitative value for an ADC for the tissue from the second NMR signal. In this embodiment, the characterization logic 894 may identify that the prostate includes the resonant species associated with PCa upon determining that the tissue has T1 in the range 1129 ms±293 ms, T2 in the range 68 ms±12 ms, or ADC in the range $390\pm203\times10^{-6}$ $mm^2/s$.

In one embodiment, the collection logic 891 collects a third NMR signal from the tissue in response to a DCE-MRI acquisition. The collection logic 891 produces a quantitative value for perfusion for the tissue from the third NMR signal. In this embodiment, the characterization logic 894 identifies that the prostate includes the resonant species associated with PCa upon determining that the tissue has T1 in the range 1129 ms±293 ms, T2 in the range 68 ms±12 ms, or perfusion within a specified range.

In one embodiment, the collection logic 891 may collect both the ADC and perfusion values. In this embodiment, the characterization logic 894 identifies that the prostate includes the resonant species associated with PCa upon determining that the tissue has T1 in the range 1129 ms±293 ms, T2 in the range 68 ms±12 ms, ADC in the range $390\pm203\times10^{-6}$ $mm^2/s$, and perfusion within a specified range.

The apparatus 800 includes a basic field magnet(s) 810 and a basic field magnet supply 820. Ideally, the basic field magnets 810 would produce a uniform B0 field. However, in practice, the B0 field may not be uniform, and may vary over an object being analyzed by the MR apparatus 800. MR apparatus 800 may include gradient coils 830 that emit gradient magnetic fields like $G_S$, $G_P$ and $G_R$. The gradient coils 830 may be controlled, at least in part, by a gradient coils supply 840. In some examples, the timing, strength, and orientation of the gradient magnetic fields may be controlled, and thus selectively adapted, during an MR procedure.

MR apparatus 800 may include a set of RF antennas 850 that generate RF pulses and receive resulting NMR signals from an object to which the RF pulses are directed. In some examples, how the pulses are generated and how the resulting MR signals are received may be controlled and thus may be selectively adapted during an MR procedure. Separate RF transmission and reception coils can be employed. The RF antennas 850 may be controlled, at least in part, by a set of RF transmission units 860. An RF transmission unit 860 may provide a signal to an RF antenna 850.

The gradient coils supply 840 and the RF transmission units 860 may be controlled, at least in part, by a control computer 870. In one example, the control computer 870 may be programmed to control an NMR device as described herein. Conventionally, the MR signals received from the RF antennas 850 can be employed to generate an image and thus may be subject to a transformation process like a two dimensional FFT that generates pixilated image data. The transformation can be performed by an image computer 880 or other similar processing device. The image data may then be shown on a display 890.

While FIG. 8 illustrates an example MR apparatus 800 that includes various components connected in various ways, it is to be appreciated that other MR apparatus may include other components connected in other ways.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 9:
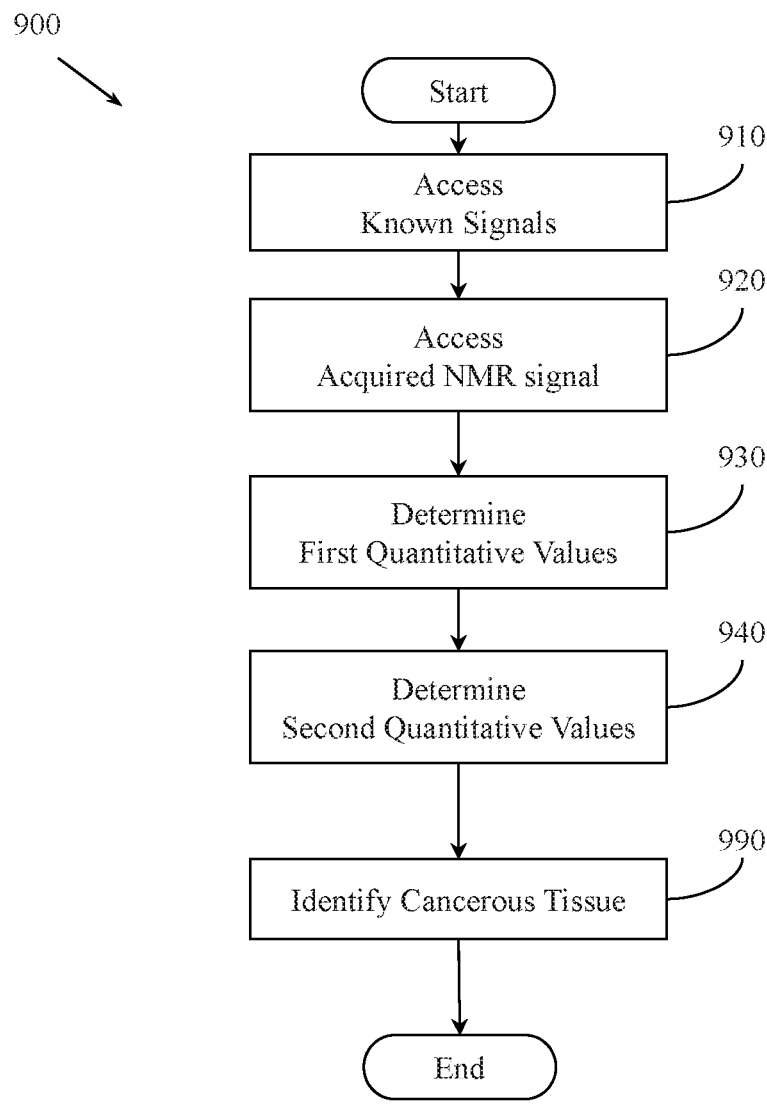
FIG. 9 illustrates an example method associated with quantitative prostate cancer imaging using MRF and another MRI technique(s).

FIG. 9 illustrates a method 900 associated with quantitative analysis of prostate tissue using MRF. Method 900 includes, at 910, accessing a set of known MRF signal evolutions. A member of the set of known MRF signal evolutions combines data associated with NMR signals associated with a plurality of resonant tissues. The stored signals and information derived from reference signal evolutions may be associated with a potentially very large data space. The data space for signal evolutions can be partially described by the MRF dictionary equations 1-8. Thus, in one embodiment, the set of known signal evolutions includes a signal selected from a set of signals described by the MRF dictionary equations. The set of known signal evolutions includes signal evolutions outside the set of signal evolutions characterized by:

$$SE = A - Be^{-t/c}$$

where:

SE is a signal evolution, A is a constant, B is a constant, t is time, and C is a single relaxation parameter.

Method 900 also includes, at 920, accessing an acquired NMR signal. In one embodiment, the acquired NMR signal is produced by a portion of a human prostate that contains one or more resonant tissues. The one or more resonant tissues simultaneously produce individual NMR signals in response to MRF excitation produced by an MRF-FISP sequence.

Method 900 also includes, at 930, selectively determining first quantitative values for T1 of the one or more resonant tissues. The first quantitative values are determined based, at least in part, on a comparison of the acquired NMR signal to the set of known MRF signal evolutions.

Method 900 also includes, at 940, selectively determining second quantitative values for T2 of the one or more resonant tissues. The second quantitative values are determined based, at least in part, on a comparison of the acquired NMR signal to the set of known MRF signal evolutions.

Method 900 also includes, at 950, identifying cancerous tissue in the human prostate as a function of the first quantitative values or the second quantitative values. The function may consider the first quantitative values and the second quantitative values with different weights. For example, the first quantitative values may be more heavily weighted and the second quantitative values may be less heavily weighted, or vice versa. In one embodiment, the weights for one type of quantitative value may be zero. Different identifications may be based on different values.

While FIG. 9 illustrates various actions occurring in serial, it is to be appreciated that various actions illustrated in FIG. 9 could occur substantially in parallel. By way of illustration, a first process could control accessing known signals, a second process could control acquiring NMR signals, a third process could determine quantitative values, and a fourth process could identify cancerous tissue. While four processes are described, it is to be appreciated that a greater and/or lesser number of processes could be employed.

Figure 10:
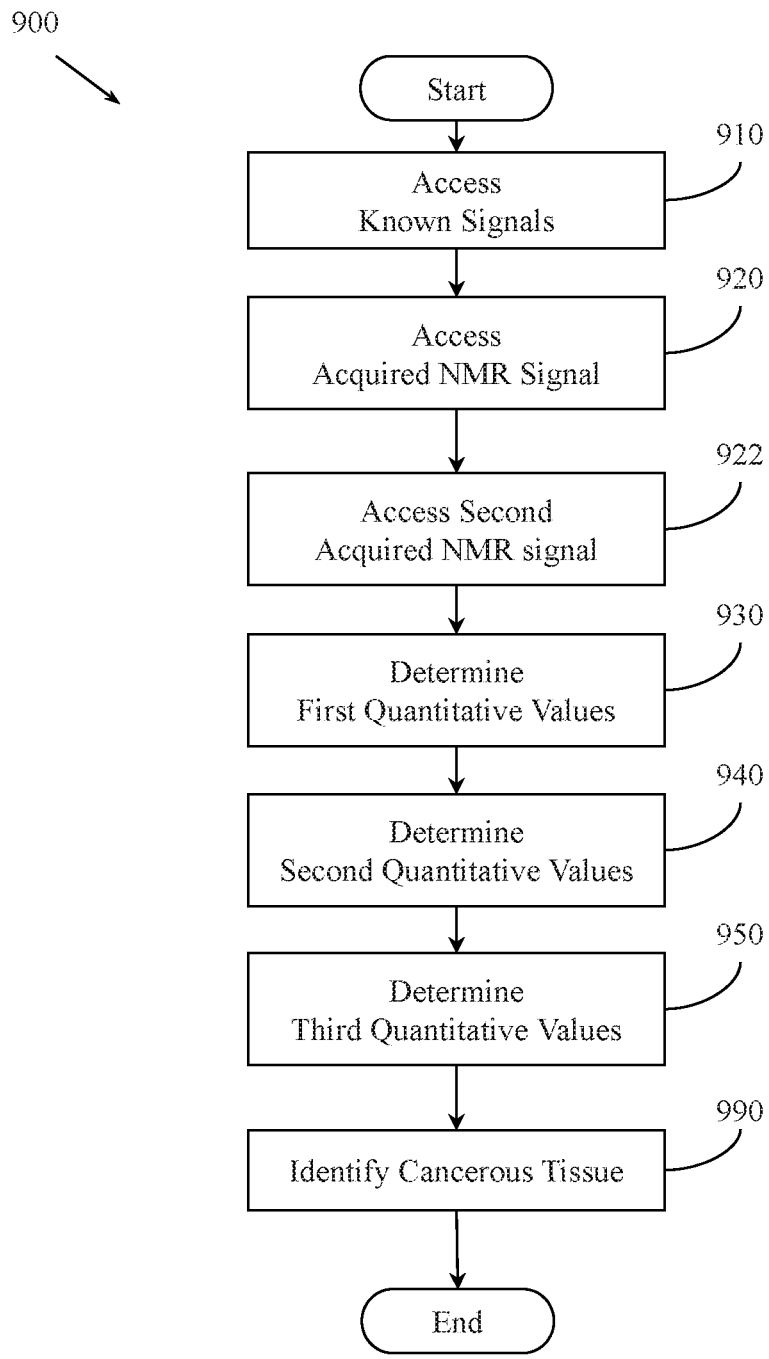
FIG. 10 illustrates an example method associated with quantitative prostate cancer imaging using MRF and another MRI technique(s).

FIG. 10 illustrates another embodiment of method 900 (FIG. 9). This embodiment includes actions 910, 920, 930, 940, and 990. However, this embodiment also includes actions 922 and 950.

Action 922 involves accessing a second acquired NMR signal produced by the portion of the human prostate. The second acquired NMR signal may have been produced in response to a DWI-MRI pulse sequence applied to the portion.

Action 950 involves determining third quantitative values for an ADC of the one or more resonant tissues from the second acquired NMR signal. In this embodiment, identifying cancerous tissue in the human prostate may be a function of the first quantitative values and the second quantitative values, the first quantitative values and the third quantitative values, the second quantitative values and the third quantitative values, or the first quantitative values, the second quantitative values and the third quantitative values.

In this embodiment, identifying cancerous tissue in the human prostate at 990 is a function of the first quantitative values, the second quantitative values, or the third quantitative values. For example, the identification may be based on T1, T2, ADC, T1 and ADC, T2 and ADC, T1 and T2, or T1, T2, and ADC. In one embodiment, tissue having T1 in the range 1129 ms±293 ms, T2 in the range 68 ms±12 ms, and ADC in the range 390±203×$10^{-6}$ mm$^2$/s is identified as cancerous tissue. In another embodiment, tissue having T2 in the range 68 ms±12 ms, and ADC in the range 390±203× $10^{-6}$ mm$^2$/s is identified as cancerous tissue.

Method 900 may also include, creating the collection of stored entries or producing the set of known MRF signal evolutions. Producing the set of known MRF signal evolutions may include combining data associated with NMR signals associated with two or more resonant species using a weighted sum operation. In one embodiment, producing the set of known MRF signal evolutions includes producing data associated with NMR signals by constraining first and second MR parameters associated with different resonant species. In one embodiment, producing the data includes varying a first MR parameter associated with a first resonant species contributing to the NMR signals while holding constant a second MR parameter associated with a second resonant species contributing to the NMR signals. In one embodiment, holding a parameter constant may include allowing the parameter to vary within a tight range (e.g., 1%, 5%) around a central value. The parameters may include T1 and T2. The first resonant species may include, for example, cells found in a human prostate. The second resonant species may include, for example, water or fluids found in a human prostate. The first resonant species may include, for example, cancerous tissues. The second resonant species may include, for example, non-cancerous tissues.

In one embodiment, producing the set of known MRF signal evolutions may include producing data associated with models of signal evolutions by holding T1 and T2 constant for a first resonant species, holding T1 and T2 constant for a second resonant species, holding T2 constant for a third resonant species, and varying T1 for the third resonant species. More generally, there may be X parameters for the Y resonant species. The Y resonant species have the same X parameters. Producing the set of known MRF signal evolutions may include fixing one of the X parameters and sweeping through or varying other of the X parameters. In one embodiment, other X parameters may be varied while in another embodiment a subset of interesting X parameters may be varied.

Figure 11:
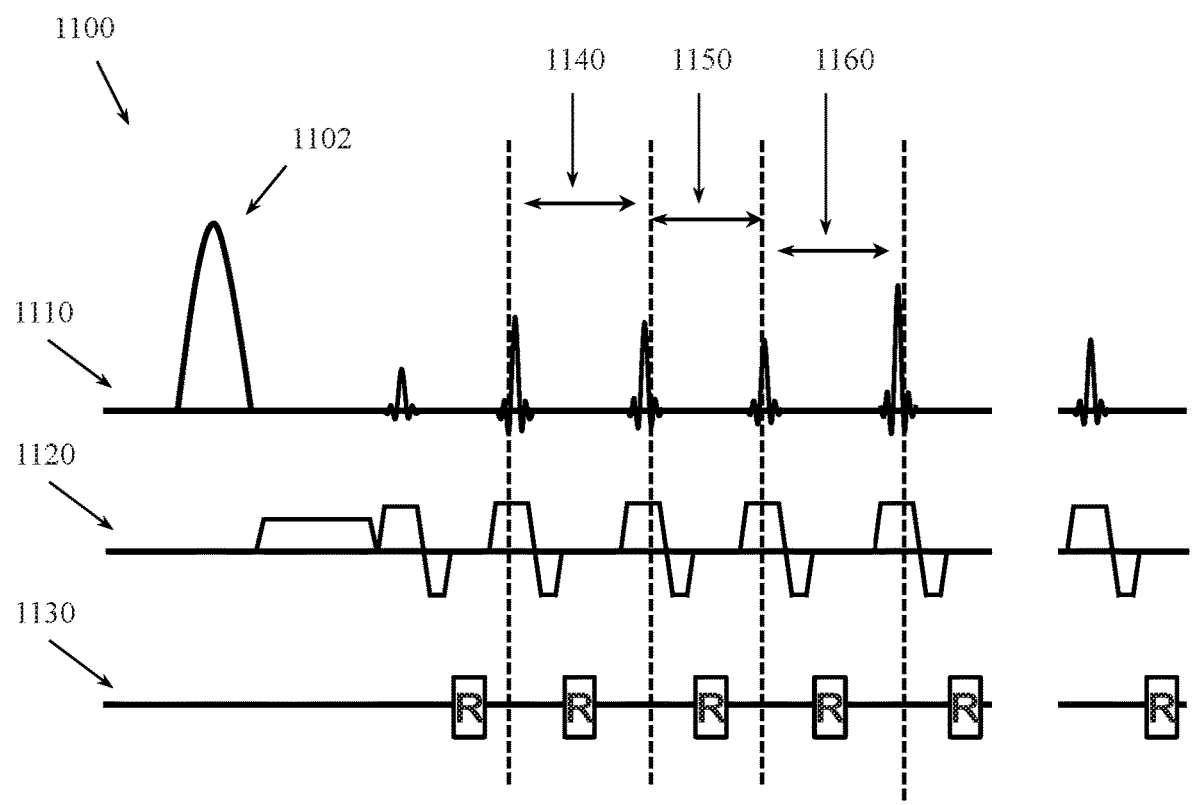
FIG. 11 illustrates an example MRF-FISP pulse sequence.
Figure 12:
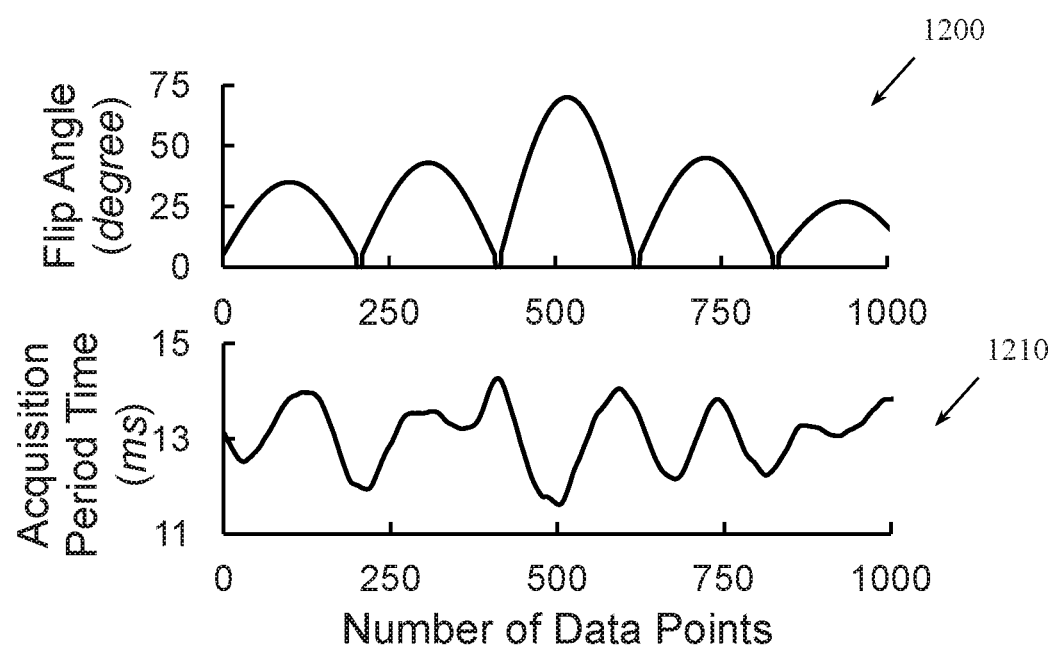
FIG. 12 illustrates data associated with an example MRF-FISP pulse sequence.
Figure 13:
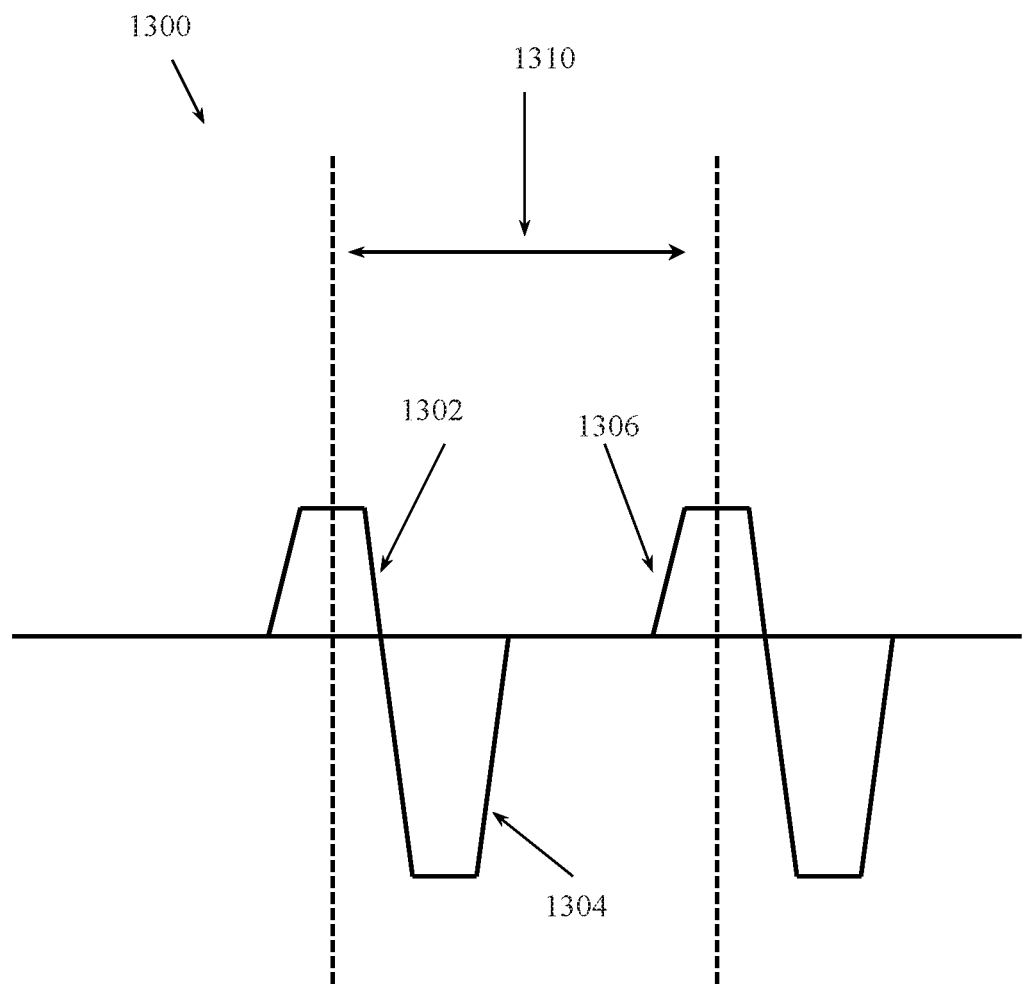
FIG. 13 illustrates a portion of an example MRF-FISP pulse sequence.

Method 900 may also include controlling the MRF apparatus to produce the MRF excitation using an MRF-FISP pulse sequence. Producing the MRF excitation is performed by applying RF energy to the volume in the object in a series of variable sequence blocks. Recall that an MRF sequence block includes one or more excitation phases, one or more readout phases, and one or more waiting phases. Recall also that at least one member of the series of variable sequence blocks differs from at least one other member of the series of variable sequence blocks in one or more sequence block parameters. Example MRF-FISP pulse sequences are illustrated in FIGS. 11-13.

In one embodiment, the NMR apparatus may vary a flip angle associated with the MRF pulse sequence or may vary the acquisition period in the MRF pulse sequence. Producing the MRF excitation may also include varying other sequence block parameters including, but not limited to, echo time, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, an amount by which a gradient is unbalanced when applied between an excitation portion of a sequence block and a readout portion of a sequence bock, a type of gradient applied between a readout portion of a sequence block and an excitation portion of a sequence block, a number of gradients applied between a readout portion of a sequence block and an excitation portion of a sequence block, an amount by which a gradient is unbalanced when applied between a readout portion of a sequence block and an excitation portion of a sequence bock, a type of gradient applied during a readout portion of a sequence block, number of gradients applied during a readout portion of a sequence block, amount of RF spoiling, or an amount of gradient spoiling.

Producing the MRF excitation may also include controlling the MRF apparatus to vary the amount of time between sequence blocks in the series of variable sequence blocks, the relative amplitude of RF pulses in sequence blocks in the series of variable sequence blocks, or the relative phase of RF pulses in sequence blocks in the series of variable sequence blocks.

Example apparatus and methods simultaneously acquire quantitative data concerning MR parameters for resonant species in an object using MRF-FISP. Example MRF-FISP apparatus and methods perform rapid quantification of multiple relaxation parameters in a manner that is less sensitive to inhomogeneity in the main magnetic field B0. The MRF-FISP pulse sequence is less sensitive to the inhomogeneity, at least in part, because the MRF-FISP sequence has unbalanced gradient moments in between RF pulses. The unbalanced gradient moments make the sequence more immune to B0 inhomogeneity due, at least in part, to controlling transverse magnetization dephasing. The increased immunity to B0 inhomogeneity improves over conventional systems by increasing the ability to add sensitivity to additional parameters including diffusion and perfusion.

FIG. 11 illustrates an example MRF-FISP pulse sequence 1100. The MRF-FISP pulse sequence 1100 includes a radio frequency (RF) inversion pulse 1102 in the RF energy 1110 applied. While an inversion pulse 1102 is illustrated, in different embodiments there may or may not be an inversion recovery period. The MRF-FISP pulse sequence 1100 includes an unbalanced slice select gradient 1120. While slice select gradient 1120 is illustrated as being unbalanced, in different embodiments other gradients (e.g., x, y, z, phase encoding, frequency encoding, readout encoding) may be unbalanced. The unbalanced slice select gradient 1120 dephases transverse magnetization produced during MRF of the object. In one embodiment, other than T2 or T2* decay, only the unbalanced slice select gradient 1120 dephases the transverse magnetization. Controlling the dephasing of transverse magnetization in this manner improves immunity to artifacts or other distortions caused by an imperfect B0. In the MRF-FISP pulse sequence 1100, the acquisition periods 1140, 1150, and 1160 do not have to be of equal duration. However, in one preferred embodiment, the acquisition periods 1140, 1150, and 1160 will be equal.

FIG. 13 illustrates a portion of an MRF-FISP pulse sequence 1300. One acquisition period 1310 is illustrated. The area 1302 usually cancels the area 1304 leaving the area 1306 as residual.

The MRF-FISP algorithm can be manipulated to generate different contrasts by varying flip angles or acquisition periods used in the MRF-FISP pulse sequence 1100. Thus, in one embodiment, to generate unique signal shapes for different tissue types that may be examined using MRF-FISP, example apparatus and methods may vary flip angle or acquisition time in different acquisition periods. In one embodiment, a flip angle or repetition time may be varied from one acquisition period to the next.

FIG. 12 illustrates one example manipulation of flip angle 1200 and acquisition time 1210 in an example MRF-FISP pulse sequence. In one embodiment, a sinusoidal variation of flip angles and acquisition times per acquisition period may be employed in a Perlin noise pattern.

The unbalanced gradient 1120 illustrated in pulse sequence 1100 (FIG. 11), combined with the variations in flip angle 1200 and acquisition period 1210 illustrated in FIG. 12 produced $2\pi$ dephasing within one voxel. Achieving $2\pi$ dephasing or more within one voxel makes data acquired using the MRF-FISP sequence more insensitive to B0 inhomogeneity. While $2\pi$ dephasing is described, other dephasing (e.g., $8\pi$) may be employed.

Figure 14:
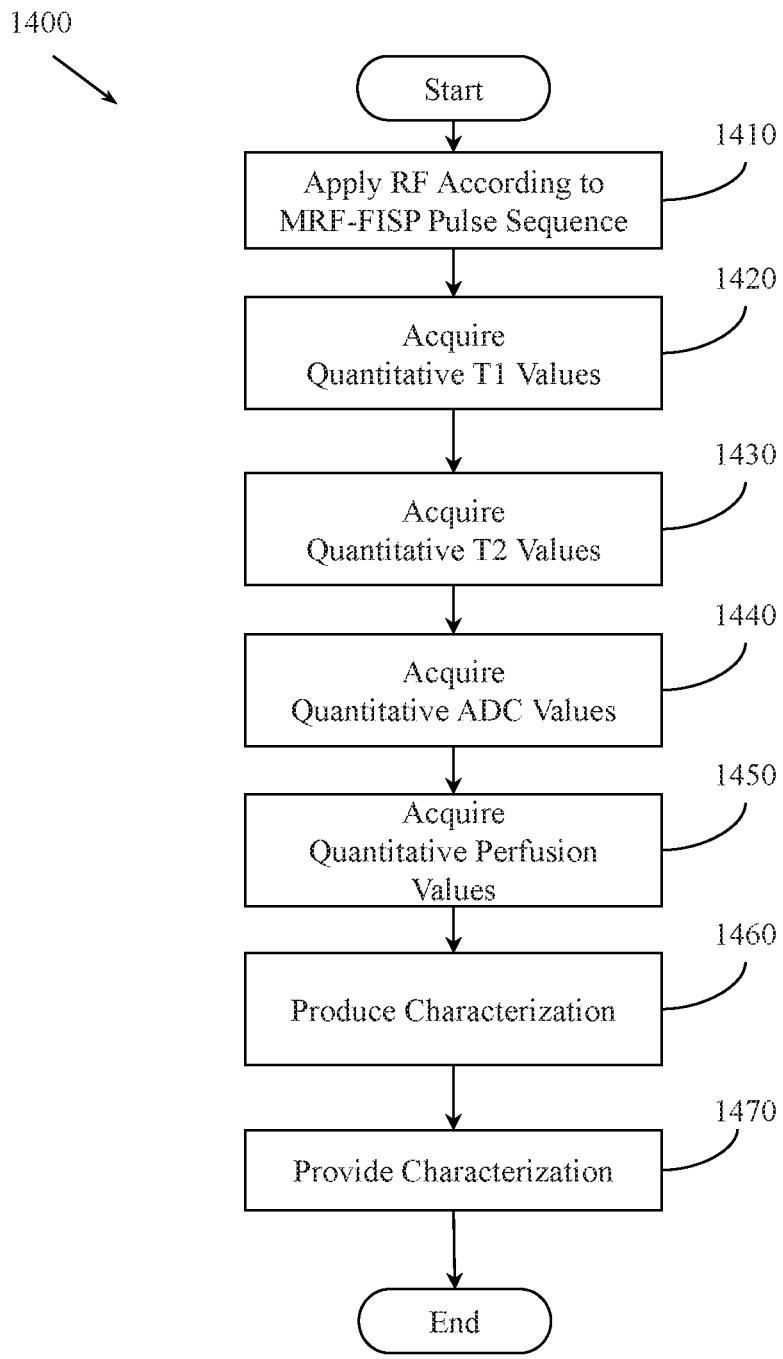
FIG. 14 illustrates an example method associated with quantitative prostate cancer imaging using MRF and another MRI technique(s).

FIG. 14 illustrates a method 1400 associated with quantitative prostate cancer analysis using MRF in combination with another MRI technique. Method 1400 facilitates non-invasively characterizing tissue. Method 1400 includes, at 1410, applying RF energy to a volume according to an MRF-FISP pulse sequence. The volume may be, for example, a human prostate.

Method 1400 also includes, at 1420, acquiring quantitative T1 values for locations in the volume. The quantitative T1 values are produced in response to the MRF-FISP pulse sequence being applied to the volume.

Method 1400 also includes, at 1430, acquiring quantitative T2 values for locations in the volume. The quantitative T2 values are produced in response to the MRF-FISP pulse sequence being applied to the volume.

Method 1400 also includes, at 1440, acquiring quantitative ADC values for locations in the volume. The quantitative ADC values may have been produced in response to a first NMR acquisition of signals from the volume. The first NMR acquisition may have been, for example, a DWI-MRI acquisition.

Method 1400 also includes, at 1450, acquiring quantitative perfusion values for locations in the volume. The quantitative perfusion values may have been produced in response to a second NMR acquisition of signals from the volume. The second NMR acquisition may have been, for example, a DCE-MRI acquisition.

Method 1400 also includes, at 1460, producing a characterization of the volume based on a combination of the quantitative T1 values, the quantitative T2 values, the quantitative ADC values, and the quantitative perfusion values. In different examples, different combinations of the quantitative values may be employed. For example, one combination may include just T2 and ADC values while another combination may include T1 and perfusion values. In one embodiment, the quantitative T1 values and quantitative T2 values are produced from NMR signals acquired simultaneously from the volume. In one embodiment, the quantitative T1 values, quantitative T2 values, and quantitative ADC values are produced from NMR signals acquired simultaneously from the volume.

In one embodiment, the characterization identifies the presence of a cancerous tissue in the volume. In one embodiment, the characterization identifies the grade of the cancerous tissue in the volume. The characterization may rely on different combinations of T1, T2, ADC, and perfusion. In one example, the characterization may identify tissue having T1 in the range 1129 ms±293 ms, T2 in the range 68 ms±12 ms, and ADC in the range $390\pm203\times10^{-6}$ mm$^2$/s as being PCa tissue. In another example, the characterization may identify tissue having T2 in the range 68 ms±12 ms, and ADC in the range $390\pm203\times10^{-6}$ mm$^2$/s as being PCa tissue. In another example, the characterization identifies tissue having T1 in the range 1576 ms±318 ms and ADC in the range $0.896\pm0.298\times10^{-3}$ mm$^2$/s as being a low grade PCa tumor. In yet another example, the characterization identifies tissue having T1 in the range 1733 ms-855 ms and ADC in the range $0.987$-$0.269\times10^{-3}$ mm$^2$/s as being a high or intermediate grade PCa tumor.

Method 1400 also includes, at 1470, providing the characterization. In one embodiment, providing the characterization may include producing a quantitative multi-parametric map from a combination of quantitative T1 values, quantitative T2 values, quantitative ADC values, and quantitative perfusion values. Once the multi-parametric map has been produced, providing the characterization at 1470 may include displaying an image associated with the quantitative multi-parametric map.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is inclusive in a manner similar to the term "comprising" as that term is interpreted when employed as a transitional word in a claim.

To the extent that the term "or" is employed in the detailed description or claims (e.g., A or B) it means "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A non-transitory computer-readable medium storing computer-executable instructions that when executed by a computer control the computer to perform a method for non-invasively characterizing tissue, comprising:
    applying radio frequency (RF) energy to a volume according to a magnetic resonance fingerprinting, fast imaging with steady state precision (MRF-FISP) pulse sequence;
    acquiring quantitative T2 values for locations in the volume, where the quantitative T2 values are produced in response to the MRF-FISP pulse sequence being applied to the volume, T2 being spin-spin relaxation;
    acquiring quantitative apparent diffusion co-efficient (ADC) values for locations in the volume, where the quantitative ADC values were produced in response to a first nuclear magnetic resonance (NMR) acquisition of signals from the volume;
    producing a characterization of the volume based on a combination of the quantitative T2 values and the quantitative ADC values; and
    providing the characterization.

2. The non-transitory computer-readable medium of claim 1, where the characterization identifies the presence of a cancerous tissue in the volume.

3. The non-transitory computer-readable medium of claim 2, the method comprising:
    acquiring quantitative T1 values for locations in the volume, where the quantitative T1 values are produced in response to the MRF-FISP pulse sequence being applied to the volume, T1 being spin-lattice relaxation; and
    where the characterization identifies the grade of the cancerous tissue in the volume.

4. The non-transitory computer-readable medium of claim 3, where the volume is a human prostate.

5. The non-transitory computer-readable medium of claim 3, where the characterization identifies tissue having T1 in a first specified T1 range, having T2 in a first specified T2 range, and having ADC in a first specified ADC range as being prostate cancer (PCa) tissue.

6. The non-transitory computer-readable medium of claim 5, where the first specified T1 range is 1157 ms±324ms, where the first specified T2 range is 70 ms±20 ms, and the first specified ADC range is $805\pm342\times10^{-6}$ mm$^2$/s.

7. The non-transitory computer-readable medium of claim 1, where the characterization identifies tissue having T2 in a first specified T2 range, and having ADC in a first specified ADC range as being prostate cancer (PCa).

8. The non-transitory computer-readable medium of claim 5, where the first specified T2 range is 70 ms±20 ms, and the first specified ADC range is $805\pm342\times10^{-6}$mm$^2$/s.

9. The non-transitory computer-readable medium of claim 3, where the characterization identifies tissue having T1 in a first specified T1 range and having ADC in a first specified ADC range as being a low grade PCa tumor .

10. The non-transitory computer-readable medium of claim 9, where the first specified T1 range is 1539 ms±376 ms and the first specified ADC range is 1.065±0.324×10$^{-3}$ mm$^2$/s.

11. The non-transitory computer-readable medium of claim 3, where the characterization identifies tissue having T1 in a first specified T1 range and ADC in a first specified ADC range as being a high or intermediate grade PCa tumor.

12. The non-transitory computer-readable medium of claim 11, where the first specified T1 range is 1297 ms-448 ms and the first specified ADC range is 0.545-0.282×10$^{-3}$ mm$^2$/s.

13. The non-transitory computer-readable medium of claim 1, where quantitative T1 values and the quantitative T2 values are produced from NMR signals acquired simultaneously from the volume.

14. The non-transitory computer-readable medium of claim 1, where quantitative T1 values, the quantitative T2 values, and the quantitative ADC values are produced from NMR signals acquired simultaneously from the volume.

15. The non-transitory computer-readable medium of claim 1, the method comprising:

acquiring quantitative perfusion values for locations in the volume, where the quantitative perfusion values were produced in response to a second NMR acquisition of signals from the volume; and producing the characterization of the volume based on a combination of quantitative T1 values, the quantitative T2 values, the quantitative ADC values, and the quantitative perfusion values.

16. The non-transitory computer-readable medium of claim 15, the method comprising:

producing a quantitative multi-parametric map from a combination of quantitative T1 values, quantitative T2 values, quantitative ADC values, and quantitative perfusion values, and displaying an image associated with the quantitative multi-parametric map.

17. The non-transitory computer-readable medium of claim 1, where the first NMR acquisition is a diffusion weighted magnetic resonance imaging acquisition.

18. The non-transitory computer-readable medium of claim 15, where the second NMR acquisition is a dynamic contrast enhanced magnetic resonance imaging acquisition.

* * * * *